United States Patent [19]
McLaughlin et al.

[11] Patent Number: 5,717,113
[45] Date of Patent: Feb. 10, 1998

[54] BIOACTIVE ACETOGENINS AND DERIVATIVES

[75] Inventors: Jerry L. McLaughlin; Zhe-ming Gu; Geng-xian Zhao, all of West Lafayette, Ind.

[73] Assignee: Purdue Research Foundation, West Lafayette, Ind.

[21] Appl. No.: 679,005

[22] Filed: Jul. 12, 1996

Related U.S. Application Data

[62] Division of Ser. No. 259,383, Jun. 14, 1994, Pat. No. 5,536,848.
[51] Int. Cl.$^6$ ............... C07D 321/10; C07D 321/12; C07D 323/00
[52] U.S. Cl. ............... 549/347; 549/320; 549/323; 549/357; 549/430
[58] Field of Search ............... 549/320, 323, 549/347, 357, 430

[56] References Cited

U.S. PATENT DOCUMENTS

| | | | |
|---|---|---|---|
| 4,721,727 | 1/1988 | Mikolajczak et al. | 514/473 |
| 4,855,319 | 8/1989 | Mikolajczak et al. | 514/473 |
| 5,229,419 | 7/1993 | McLaughlin et al. | 514/473 |
| 5,536,848 | 7/1996 | McLaughlin et al. | 549/320 |

OTHER PUBLICATIONS

Rupprecht, J. Kent et al., "Annonaceous Acetogenins: A Review", Mar–Apr. 1990, *Journal of Natural Products*, vol. 53, No. 2, pp. 237–278.

Fang, Xin–ping et al.,"Annonaceous Acetogins: An Updated Review and Appendices", 1993, *Phytochemical Analysis*, vol. 4, pp. 27–67.

Fang, Xin–ping et al., "A New Type of Cytotoxic Annonaceous Acetogenin: Giganin from Goniothalamus Giganteus", 1993, *Bioorganic & Medicinal Chem. Letters*, vol. 3, No. 6, pp. 1153–1156.

Gu, Zhe–ming et al., "New Cytotoxic Annonaceous Acetogenins: Bullatanocin and cis–trans–Bullatanocinone From Annona Bullata (Annonaceae)", 1993, *Tetrahedron*. vol. 49, p. 747.

Gu, Zhe–ming et al., "Bullacin: A New Cytotoxic Annonaceous Acetongenin From Annona Bullata", 1993, *Heterocycles*, vol. 36, No. 10, pp. 2221–2228.

Gu, Zhe–ming et al., "30–, 31–, and 32–Hydroxybullatacinones: Bioactive Terminally Hydroxylated Annonaceous Acetongenins from Annona Bullata", Jun. 1993, *Journal of Natural Products*, vol. 56, No. 6, pp. 870–876.

*Primary Examiner*—Ba K. Trinh
*Attorney, Agent, or Firm*—Barnes & Thornburg

[57] ABSTRACT

Novel acetogenins isolated from *Asimina triloba* and *Goniothalamus giganteus* of the family Annonaceae and derivatives of those and other acetogenins are described. Bioactive cyclic formaldehyde acetal derivatives are prepared from Annonaceous acetogenins having 1,2-, 1,4- or 1,5-diols. A non-adjacent bis-tetrahydrofuran (THF) acetogenin is prepared from an unsaturated mono-THF acetogenin earlier isolated from *Goniothalamus giganteus*. The substantially pure acetogenins and acetogenin derivatives of the invention exhibit cytotoxicity to human solid tumor cell lines equipotent to adriamycin or orders of magnitude more potent than adriamycin, and they exhibit effective pesticidal activities.

2 Claims, No Drawings

BIOACTIVE ACETOGENINS AND DERIVATIVES

This is a division of application Ser. No. 08/259,383, filed Jun. 14, 1994 now U.S. Pat. No. 5,536,848.

FIELD OF INVENTION

This invention relates to the isolation, identification, derivatization, and use of natural products. More particularly this invention is directed to substantially pure forms of cytotoxic Annonaceous acetogenins and certain ester and cyclized ether acetogenin derivatives.

BACKGROUND AND SUMMARY OF THE INVENTION

In recent years, an increased interest in the phytochemistry of the Annonaceae has been sparked by the bioactivity-directed isolation of the antileukemic Annonaceous acetogenin, uvaricin, from *Uvaria acuminata*. Acetogenins are $C_{35}$–$C_{39}$ compounds and typically contain two long hydrocarbon chains, one of which connects a terminal 2,4-disubstituted-γ-lactone to a variable number of tetrahydrofuran (THF) rings. The hydrocarbon chains contain a number of oxygenated moieties which can be hydroxyls, acetoxyls and/or ketones. Recently, single-ring acetogenins containing double bonds, epoxide compounds which lack THF rings and a compound lacking both epoxides and THF rings have been reported. These interesting newer compounds support the proposed polyketide origin of the Annonaceous acetogenins and provide additional clues to their biogenesis.

All acetogenins found to date contain multiple stereocentres, the elucidation of which often presents daunting stereochemical problems. Because of their waxy nature, the acetogenins do not produce crystals suitable for X-ray crystallographic analysis. Relative stereochemistries of ring junctions have typically been determined by comparison of natural compounds with synthetic model compounds and such methods have proven to be invaluable with the acetogenins. Recently, the absolute stereochemistries of the carbinol centers of acetogenins have been determined with the help of synthetic model compounds and high field nuclear magnetic resonance (NMR) analysis of their methoxyfluoromethylphenylacetic acid (MPTA) esters (Mosher esters).

Most Annonaceous acetogenins are potently bioactive, but the mode of action of these compounds was unknown until Londerhausen et al. concluded in *Pesticide Science*, 33,427–438 (1991), that they act to inhibit complex I of mitochondrial oxidative phosphorylation with an activity several times that of rotenone.

In accordance with the present invention there are provided novel, cytotoxic acetogenins and acetogenin derivatives. One group of acetogenins of this invention isolated from *Asimina triloba* are represented by the general formula

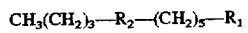

wherein $R_1$ is a group of the formula

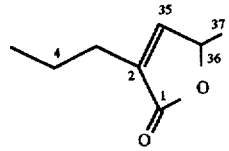

and $R_2$ is a divalent group selected from the group consisting of

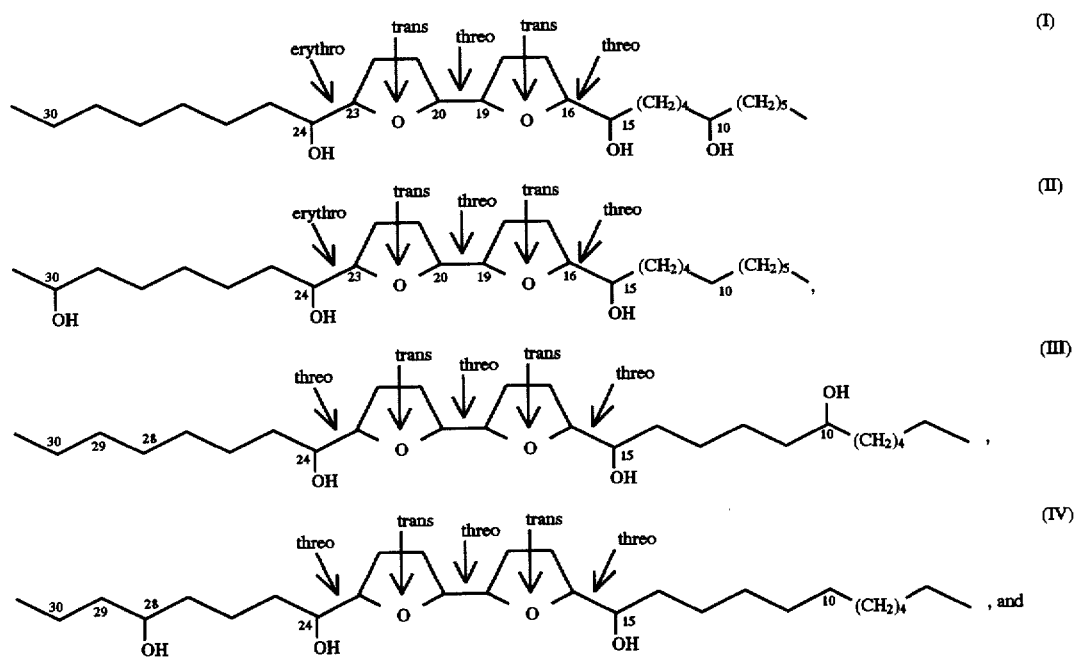

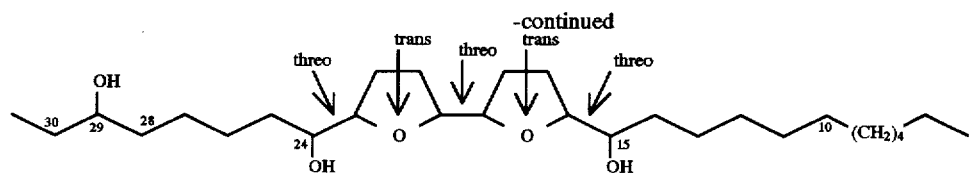

and acetylated derivatives thereof.

Another embodiment of this invention provides substantially pure compounds of the formula $$CH_3(CH_2)_{11}—R_3—(CH_2)_5R_1'$$

wherein $R_1'$ is a group of the formula

and $R_3$ is selected from

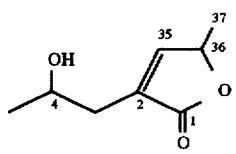

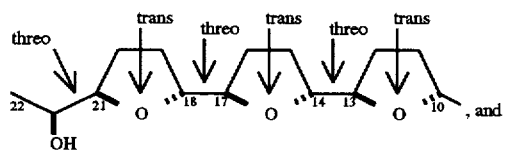

and acetylated derivatives thereof. The compound wherein —$R_3$— is the divalent group (VI) is denominated goniocin, a naturally occurring acetogenin isolated from *Goniothalamus giganteus*. The compound wherein —$R_3$— is the divalent group (VII) is prepared by epoxidation and subsequent acid-catalyzed cyclization of a previously reported acetogenin, gigantetronenin (also isolated from *Goniothalamus giganteus*), having the above formula wherein —$R_3$— is a divalent group of the formula

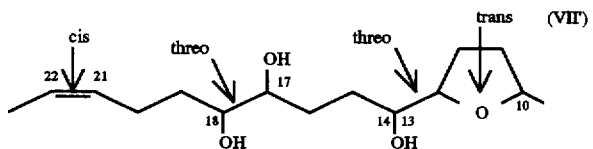

Another aspect of this invention is directed to novel cyclic formaldehyde acetal derivatives of acetogenins having at least one 1,2-diol, 1,4-diol and/or 1,5-diol moiety in their structure. Such acetogenins include the art-recognized acetogenins bullatalicin, bullatanocin, squamocin, squamostatin A, gigantetrocin and goniothalamicin. The cyclic intramolecular formaldehyde acetal derivatives are prepared by reacting the acetogenin starting material with a 2–3 fold molar excess of chlorotrimethylsilane and dimethyl sulfoxide. Bis-cyclic formaldehyde acetals can be formed from acetogenins having two independent 1,2-, 1,4-, or 1,5-diol moieties. Preparation of the cyclic acetals significantly facilitates stereochemical structure elucidation. Moreover, the acetal derivatives show enhanced cytotoxicities against certain human tumor cell lines. The enhancement of the bioactive potencies and selectivities can permit improved utilization of many natural acetogenins.

The present invention further provides pharmaceutical formulations comprising an effective amount of a acetogenin compound for treating a patient having a tumor. As used herein, an effective amount of the acetogenin compound is defined as the amount of the compound which, upon administration to a patient, inhibits growth of tumor cells, kills malignant cells, reduces the volume or size of the tumors or eliminates the tumor entirely in the treated patient. Thus, the substantially pure compounds in accordance with this invention can be formulated into dosage forms using pharmaceutically acceptable carriers for oral or parenteral administration to patients in need of oncolytic therapy.

The effective amount to be administered to a patient is typically based on body surface area, patient weight, and patient condition. The interrelationship of dosages for animals and humans (based on milligrams per meter squared of body surface) is described by Freireich, E. J., et al., *Cancer Chemother. Rep.*, 50 (4): 219 (1966). Body surface area may be approximately determined from patient height and weight (see e.g., Scientific Tables, Geigy Pharmaceuticals, Ardley, N.Y., pages 537–538 (1970)). Preferred dose levels will also depend on the attending physicians' assessment of both the nature of the patient's particular cancerous condition and the overall physical condition of the patient. Effective antitumor doses of the present acetogenin compounds range from about 1 microgram per kilogram to about 200 micrograms per kilogram of patient body weight, more preferably between about 2 micrograms to about 100 micrograms per kilogram of patient body weight.

Effective doses will also vary, as recognized by those skilled in the art, dependant on route of administration, excipient usage and the possibility of co-usage with other therapeutic treatments including other anti-tumor agents, and radiation therapy.

The present pharmaceutical formulation may be administered via the parenteral route, including subcutaneously, intraperitoneally, intramuscularly and intravenously. Examples of parenteral dosage forms include aqueous solutions of the active agent, in a isotonic saline, 5% glucose or other well-known pharmaceutically acceptable liquid carrier. In one preferred aspect of the present embodiment, the acetogenin compound is dissolved in a saline solution containing 5% of dimethyl sulfoxide and 10% Cremphor EL (Sigma Chemical Company). Additional solubilizing agents such as cyclodextrins, which form specific, more soluble complexes with the present acetogenin compounds, or other solubilizing agents well-known to those familiar with the art, can be utilized as pharmaceutical excipients for delivery of the acetogenin compounds. Alternatively, the present compounds can be chemically modified to enhance water solubility.

The present compound can also be formulated into dosage forms for other routes of administration utilizing well-known methods. The pharmaceutical compositions can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with conventional procedure by compressing mixtures of the active acetogenins and solid carriers, and lubricants well-known to those familiar with the art. Examples of solid carriers include starch, sugar, bentonite. The compounds of the present invention can also be administered in a form of a hard shell tablet or capsule containing, for example, lactose or mannitol as a binder and a conventional fillers and tableting agents.

DETAILED DESCRIPTION OF THE INVENTION

Bullatacin is one of the most potent antitumor and pesticidal Annonaceous acetogenins and was first reported and isolated from Annona bullata in 1989. The correct absolute configurations of the stereogenic carbinol centers of bullatacin were recently established by $^1$H- and $^{19}$F-NMR spectral analysis of bullatacin's (S)- and (R)-Mosher ester [methoxy (trifluoromethyl)phenylacetate or MTPA] derivatives. Bullatacin has shown potent in vivo antitumor activities, e.g., 67% tumor growth inhibition (TGI) at 50 μg/kg in athymic mice bearing A2780 human ovarian cancer xenografts. Bullatacin likely inhibits cancer cell growth through inhibition of mitochondrial electron transport systems to reduce the ATP levels. Eleven Annonaceous acetogenins have been previously reported from the ETOH extract of the stem bark of Asimina triloba. Directed by the brine shrimp lethality test (BST). Two related isomeric acetogenins, the bullatacin threo-trans-threo-trans-erythro from C-15 to C-24 isomers bullatin (1), and bullanin (2), which have the third hydroxyl group at C-10 and C-30, instead of at C-4.

Bullatin (1), a colorless wax, was obtained after HPLC separation from the more polar fractions of the 90% methanolic partition extract. The molecular weight was determined as 622 by FAB mass spectrometry based on the molecular ion peak (MH$^+$) m/z 623. The molecular formula was then deduced as $C_{37}H_{66}O_7$ by the high resolution FAB mass spectrum which gave the molecular ion at m/z 623.4865 corresponding to the calculated exact mass of 623.4887. The IR spectrum of 1 showed characteristic absorptions of the α,β-unsaturated γ-lactone (1748 cm$^{-1}$, C=O) and hydroxyl (3442 cm$^{-1}$, OH) functional groups. The presence of the α,β-unsaturated γ-lactone moiety was confirmed by the $^1$H NMR resonance peaks (Table 1) at δ6.99 (1, H-35), 5.00 (11, H-36) and $^{13}$C NMR resonances (Table 1) at δ173.83 (C-1), 134.21 (C-2), 148.85 (C-35), 77.43 (C-36), and 19.27 (C-37). Spectral comparisons of 1 with bullatacin, the 4-hydroxylated isomer, indicated that the H-3 signals appeared as a multiplet peak at δ2.26 (tt 2H) in the $^1$H NMR spectrum of 1 instead of an AB spin system corresponding to the H-3a and H-3b proton resonance in the $^1$H NMR spectrum of bullatacin, and the upfield shift of proton signals for H-35 and H-36 of compound 1 suggested that the 4-OH group was absent in the structure of bullatin (1).

Careful examination of the $^1$H NMR spectrum of 1 showed the typical proton resonances of the adjacent bis THF acetogenins. The three multiplets at δ3.41, 3.87, and 3.93 integrated for one proton, four protons and one proton, respectively, on oxygen-bearing carbons, and the $^{13}$C NMR resonances of these methine carbons at δ71.31, 73.99, 82.52, 82.33, 82.81 and 83.14 indicate the presence of the structural unit of an adjacent bis-THF moiety with two flanking OH groups. $^1$H and $^{13}$C -spectral comparisons of 1 with bullatacin suggested that the relative stereochemical relationship of 1 across the bis-THF skeleton from C-15 through C-24 is threo-trans-threo-trans-erythro, and, thus, 1 belongs to the bullatacin type acetogenins. This conclusion was confirmed by the expected downfield shift of these methine proton resonances and their locations at δ

| compounds | R$_1$ | R$_2$ | R$_3$ | R$_4$ | R$_5$ | R$_6$ | R$_7$ |
|---|---|---|---|---|---|---|---|
| bullatin (1) | H | OH | OH | OH | H | H | H |
| bullanin (2) | H | H | OH | OH | H | H | OH |

TABLE 1

$^1$H (500 MHz) and $^{13}$C (125 MHz) NMR Data of 1 and 1a

| H/C No. | $^1$H-NMR of 1 | $^1$H-NMR of 1a | $^{13}$C-NMR of 1 |
|---|---|---|---|
| 1 | — | — | 173.83 |
| 2 | — | — | 134.21 |
| 3 | 2.26 tt (7.6, 1.5) | 2.26 tt (7.6, 1.5) | 22.73–31.94 |
| 4 | 1.55 m | 1.40–1.80 m | 22.73–31.94 |
| 9, 11 | 1.43 m | 1.40–1.80 m | 37.423 37.45 |
| 10 | 3.59 m | 4.85 m | 71.85* |
| 14, 25 | 1.40 m | 1.40–1.80 m | 33.31, 33.46 |
| 15 | 3.41 m | 4.85 m | 73.99 |
| 16 | 3.87 m | 3.98 m | 83.14** |
| 17, 18, 21 | 1.98 m, 1.64 m | 1.98 m, 1.64 m | 22.73–31.94 |
| 19, 20 | 3.87 m | 3.91 m | 82.52, 82.33 |
| 22 | 1.81 m, 1.89 m | 1.80 m, 1.89 m | 22.73–31.94 |
| 23 | 3.93 m | 3.98 m | 82.81** |
| 24 | 3.87 m | 4.92 m | 71.31* |
| 5–8, 12–13, 26–33 | 1.20–1.50 m | 1.20–1.80 m | 22.73–31.94 |
| 34 | 0.878 t (7.0) | 0.878 t (7.0) | 14.18 |
| 35 | 6.99 q (1.5) | 6.99 q (1.5) | 148.85 |
| 36 | 5.00 qq (6.8, 1.8) | 5.00 qq (6.8, 1.7) | 77.43 |
| 37 | 1.41 d (7.0) | 1.41 d (7.0) | 19.27 |
| 15-OAc | | 2.08 s | |
| 24-OAc | | 2.05 s | |
| 10-OAc | | 2.04 s | |

*, **Indicate assignments which may be interchangable.

TABLE 2

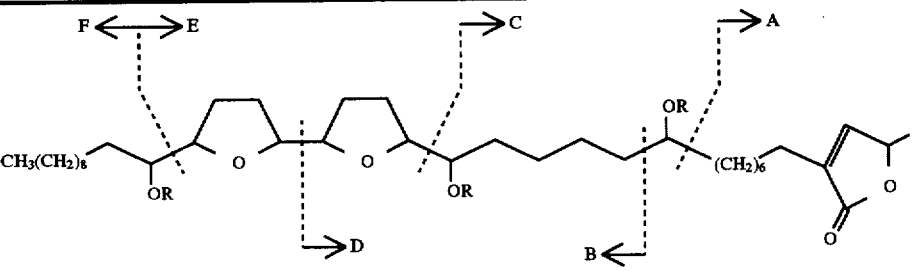

| R | A | B | C | D | E | F |
|---|---|---|---|---|---|---|
| H (EIMS) | (427) 409 (a) 391 (a) 373 (a) | 225 | 311 293 (a) 275 (a) | (381) 363 (a) 345 (a) 327 (a) | | 171 |
| TMS (EIMS) | 643 553 (b) | 297 | 455 365 (b) 275 (b) | (525) 435 (b) | 595 505 (b) 415 (b) 397 (a) | 243 |
| $D_9$-TMS (EIMS) | (670) 571 (c) 472 (c) 373 (c) | 306 | 473 374 (c) 275 (c) | (543) 444 (c) 345 (c) 327 (c) | 613 514 (c) 415 (c) 397 (a) | 252 |

(a): loss of $H_2O$ (m/z 18); (b): loss of TMSiOH (m/z 90); (c): loss of $d_9$-TMSiOH (m/z 99).

3.91, 3.98, 4.85, and 4.92 in the $^1H$ NMR spectrum of bullatin triacetate (1a).

The existence of three OH groups was determined by successive losses of three water molecules (m/z 18×3) in the EIMS spectrum of 1 (Table 2) and the three single acetate methyl proton signals, at δ2.04, 2.05 and 2.08, in the $^1H$ NMR spectrum of bullatin triacetate (1a) (Table 1). In addition to the two flanking OH groups on each side of the THF ring system there had to be a third hydroxyl in this structure and it could not be located at C-4. In the $^1H$ NMR spectrum of 1, the methine proton on the carbon to which the third hydroxyl group was attached appeared at δ3.59 and showed its only cross peak with the complex of methylene proton signals at δ1.43 in the $^1H$—$^1H$ 2D homonuclear correlation (COSY) spectrum, indicating that this third OH group was located somewhere in the aliphatic chain.

The placement of the adjacent bis-THF ring at C-16 through C-23 and the three OH groups at C-10, C-15 and C-24 in the aliphatic chain was established by the analysis of the EIMS spectra of the tri-trimethyl silyl (tri-TMS) and tri-deutero-trimethylsilyl ($d_9$-tri-TMS) derivatives of 1 (Table 2). The crucial fragment peaks at m/z 297 in the EIMS spectra of the tri-TMS derivative and m/z 306 in the EIMS spectra of the $d_9$-tri-TMS derivative of 1, due to the cleavage of the bond between C-10 and C-11, indicated that the third OH group was located at the C-10 position. This conclusion was further confirmed by the exact mass determination of these fragment ions of the tri-TMS and $d_9$-tri-TMS derivatives, i.e., for the m/z 297 ion peak the exact mass 297.1886 was found corresponding to the formula, $C_{16}H_{29}SiO_3$ (calcd. 297.1886), and for the m/z 306 ion the exact mass of 306.2451 was found corresponding to the formula of $C_{16}H_{20}D_9SiO_3$ (calcd. 306.2451). The full assignment of proton resonance signals was made by analysis of the $^1H$—$^1H$ 2D NMR (COSY) spectrum of 1. Thus, the structure of bullatin was concluded to be as indicated above.

Bullanin (2) was obtained in a waxy form. The IR, $^1H$ and $^{13}C$ NMR (Table 2), and $^1H$—$^1H$ correlation (COSY) spectra of bullanin were very similar to bullatin (1). The existence of three OH groups was indicated by the broad IR absorption peak at 3442 cm$^{-1}$ and the three acetate methyl resonances at δ2.04, 2.05 and 2.08 in the $^1H$ NMR spectrum of bullanin triacetate (2a) (Table 3). The appropriate proton and carbon resonance signals were attributed to the α,β-unsaturated γ-lactone moiety and the adjacent bis-THF ring system, as the $^1H$ and $^{13}C$ NMR spectra of bullanin showed little differences from those of bullatin (1).

The low resolution FAB mass of bullanin gave the [MH$^+$] peak at 623, indicating a molecular weight of 622. This was confirmed by the molecular ion peak at m/z 623.4915 in the high resolution FAB mass spectrum corresponding to the molecular formula $C_{37}H_{66}O_7$ (calcd. 623.4887). Thus, bullanin was identified as another isomer of bullatacin, having the same carbon skeleton and relative stereochemistries as bullatin (1) but with a different location of the third OH group. The relative stereochemistry at the six chiral centers from C-15 through C-24 across the bis-THF ring of bullanin was confirmed as threo-trans-threo-trans-erythro by the typical downfield shifts and placements of these oxygen-bearing methine proton signals in the bis-THF rings in the $^1H$ NMR spectrum of bullatacin triacetate (2a) (Table 2).

The EIMS diagnostic fragment peaks of the tri-TMS and $d_9$-tri-TMS derivatives of bullanin (Table 4) determined the positions of the adjacent bis-THF ring moiety and the third OH group. Careful analysis of the EIMS fragmentation ions of the tri-TMS and $d_9$-tri-TMS derivatives led us to conclude that, like bullatin, the bis-THF ring with two flanking OH

TABLE 3

| $^1H$ (500 MHz) and $^{13}C$ (125 MHz) NMR Data of 2 and 2a | | | |
|---|---|---|---|
| H/C No. | $^1H$-NMR of 2 | $^1H$-NMR of 2a | $^{13}C$-NMR of 2 |
| 1 | — | — | 173.83 |
| 2 | — | — | 134.23 |
| 3 | 2.26 tt (7.5, 1.5) | 2.26 tt (7.5, 1.5) | 22.80–29.76 |
| 4 | 1.54 m | 1.54 m | 22.80–29.76 |
| 14, 25 | 1.39 m | 1.46–1.64 m | 33.33, 32.27 |
| 15 | 3.40 m | 4.86 m | 74.11 |
| 16 | 3.85 m | 3.98 m | 83.25** |

TABLE 3-continued

$^1$H (500 MHz) and $^{13}$C (125 MHz) NMR Data of 2 and 2a

| H/C No. | $^1$H-NMR of 2 | $^1$H-NMR of 2a | $^{13}$C-NMR of 2 |
|---|---|---|---|
| 17, 18, 21 | 1.98 m, 1.63 m | 1.95 m, 1.78 m | 22.80–29.76 |
| 19, 20 | 3.85 m | 3.89 m | 82.52, 82.26 |
| 22 | 1.90 m, 1.81 m | 1.95 m, 1.78 m | 22.80–29.76 |
| 23 | 3.93 m | 3.98 m | 82.75** |
| 24 | 3.85 m | 4.91 m | 71.28* |
| 29, 31 | 1.40 m | 1.46–1.64 m | 37.17, 37.34 |
| 30 | 3.58 m | 4.86 m | 71.87* |
| 5–13, 26–27, 31–33 | 1.22–1.72 m | 1.20–1.38 m | 22.80–29.76 |
| 34 | 0.907 t (7.0) | 0.907 t (7.0) | 14.14 |
| 35 | 6.99 q (1.5) | 6.99 q (1.5) | 148.79 |
| 36 | 5.00 qq (7.0, 1.5) | 5.00 qq (7.0, 1.5) | 77.41 |
| 37 | 1.41 d (7.0) | 1.41 d (7.0) | 19.26 |
| 15-OAc | | 2.08 s | |
| 24-OAc | | 2.05 s | |
| 29-OAc | | 2.04 s | |

*, **Indicate assignments which may be interchangable.

groups was also located at C-15 through C-24. The hypothesis that the third OH group was placed at C-30 was confirmed by the crucial diagnostic mass ion at m/z 159 in the EIMS spectrum of the tri-TMS derivative (high resolution EIMS found: m/z 159.1203, calcd. 159.1205 for $C_8H_{19}SiO$) due to cleavage between C-29 and C-30. Confirming support for the C-30 hydroxyl was made by the mass ion at m/z 168 in the EIMS spectrum of the $d_9$-tri-TMS derivative (high resolution EIMS found: m/z 168.1771, calcd. 168.1770 for $C_8H_{10}D_9SiO$). The proton signal assignments (Table 3) were made by detailed analysis of the $^1$H—$^1$H correlated 2D spectrum (COSY). From these data, the structure of bullanin (2) was concluded to be as that shown above.

Bioactivity data obtained with 1 and 2 are summarized in Table 5. Each of these acetogenins were highly toxic to the brine shrimp larvae, showed highly potent cytotoxicities against three solid tumor cell lines, A-549 (human lung carcinoma), MCF-7 (human breast carcinoma) and HT-29 (human colon adenocarcinoma), and were several orders of magnitude more cytotoxic than the standard reference, adriamycin. The highly potent cytotoxicities of bullatacin isomers 1 and 2 suggested that the presence of a third OH group at either C-4, C-10, C-28, C-29 or C-30 is responsible for the enhancement of activity. Bullatin (2) approaches the level of potencies of bullatacin (2). In mitochondrial inhibition assays, using rat liver mitochondria, bullatacin, bullatin (1) and bullanin (2) all show high activity with bullanin (2) showing slightly higher potencies than bullatacin.

Experimental Details for Isolation and Characterization of Compounds 1 and 2

TABLE 4

| R | A | B | C | D | E | F | G | H |
|---|---|---|---|---|---|---|---|---|
| H | 295 | (327) | | (257) | (435) | 187 | | 565 |
| (EIMS) | 277 (a) | (309) | | 239 (a) | 417 (a) | 169 (a) | | (547) |
| | | 291 (a) | | 221 (a) | | 151 (a) | | (529) |
| | | | | | | | | 511 (a) |
| TMS | 367 | (471) | 437 | (401) | 507 | 331 | 159 | 781 |
| (EIMS) | | 381 (b) | 347 (b) | 311 (b) | 417 (b) | 241 (b) | | (691) |
| | | 291 (b) | 329 (a) | 293 (a) | 399 (a) | 151 (b) | | 601 (b) |
| $d_9$-TMS | 376 | (489) | (446) | 419 | 516 | 349 | 168 | (808) |
| (EIMS) | 277 (c) | 390 (c) | 347 (c) | 320 (c) | 417 (c) | 250 (c) | | |
| | | 291 (c) | 329 (a) | | 399 (a) | 151 (c) | | |

(a): loss of $H_2O$ (m/z 18); (b): loss of TMSiOH (m/z 90); (c): loss of $d_9$-TMSiOH (m/z 99).
Diagnostic EIms fragmentation ions of 2 and its tri-TMS and tri-$d_9$-TMS derivatives

TABLE 5

Bioactivity Data of Acetogenins 1–7.

| Compounds* | BST $LC_{50}(\mu g/ml)$ | A-549 $LC_{50}(\mu g/ml)$ | MCF-7 $LC_{50}(\mu g/ml)$ | HT-29 $LC_{50}(\mu g/ml)$ |
|---|---|---|---|---|
| 1 | $4.0 \times 10^{-3}$ | $9.39 \times 10^{-6}$ | $8.33 \times 10^{-6}$ | $3.78 \times 10^{-6}$ |
| 2 | $6.0 \times 10^{-3}$ | $3.11 \times 10^{-14}$ | $3.22 \times 10^{-14}$ | $4.77 \times 10^{-12}$ |
| 3 | $4.6 \times 10^{-3}$ | $7.99 \times 10^{-9}$ | $9.57 \times 10^{-9}$ | $<10^{-12}$ |
| 4 | $5.7 \times 10^{-3}$ | $3.58 \times 10^{-9}$ | $<10^{-12}$ | $<10^{-12}$ |
| 5 | $4.9 \times 10^{-3}$ | $3.29 \times 10^{-7}$ | $2.74 \times 10^{-9}$ | $<10^{-12}$ |
| Adriamycin | $2.57 \times 10^{-1}$ | $1.04 \times 10^{-4}$ | $1.76 \times 10^{-2}$ | $1.53 \times 10^{-4}$ |

*Compounds 1–5 were bioassayed as the 2/4-cis and trans mixtures; Adriamycin was included as expected variations between runs are up to two orders of magnitude as evidenced by adriamycin data on file.
BST = brine shrimp lethality test
A-549 = cytotoxicity to human lung carcinoma
MCF-7 = cytotoxicity to human breast carcinoma
HT-29 = cytotoxicity to human colon adenocarcinoma

Bioassays

The brine shrimp (Artemia salina Leach) test (BST) was performed as modified to determine $LC_{50}$ values in μg/ml. Seven-day in vitro cytotoxicity tests against human tumor cell lines were carried out at the Purdue Cancer Center, using standard protocols for A-549 (human lung carcinoma), MCF-7 (human breast carcinoma) and HT-29 (homan colon carcinoma) with adriamycin as a positive control. The reported $ED_{50}$ values in μg/ml (Table 3) were tabulated from the same run in order to facilitate comparison for the SAR's.

Plant Material

The bark of *Asimina triloba* (L.) Dunal was collected from stands growing wild at the Purdue Horticultural Research Farm, West Lafayette, Ind., U.S.A. The identification was confirmed by Dr. George R. Parker, Department of Forestry and Natural Resources, Purdue University. A voucher specimen of the bark is preserved in the pharmacognosy herbarium.

Extraction and Purification of Acetogenins

The air-dried pulverized stem bark (15 kg) was extracted exhaustively (12 days) at room temperature with 95% EtOH (45l×4) and vacuum evaporated to yield extract F001 (1645 g) which was partioned between $H_2O$ (41) and $CH_2Cl_2$ (41×5), giving a water soluble fraction (F002, 5 g), $CH_2Cl_2$ soluble fraction (F003, 1560 g) and an insoluble interface (F004, 80 g). F003 was further partioned between hexane (41) and 90% MeOH aq soln (41×5) and yielded the MeOH fraction (F005, 650 g) and the hexane fraction (F006, 905 g).

Directed by the BST bioassay, the most bioactive fraction, F005 (BST $LC_{50}$ 7.151×10$^{-1}$ μg/ml) (200 g) was further fractionated by open column chromatography on silica get (8 Kg, 60–200 mesh), eluting with hexane-EtOAc and EtOAc-MeOH gradients; 12 pools were made from the collected fractions according to their TLC patterns and evaluated by the BST bioassay. The most active pools (P$_7$–P$_9$) were combined (20 g) and subjected to further repeated separation by silica gel (1000 g, 230–400 mesh) column chromatography eluted with MeOH—CHCl$_3$ gradients. Further purifications of the most bioactive fractions F11–12 (1.2 g, BST $LC_{50}$ 3.5×10$^{-2}$ mg/ml) were carried out on Chromatotron plates (2 mm thick), eluted with hexane-$CH_2Cl_2$—MeOH (30:20:0–5). A white wax from the hexane-$CH_2Cl_2$—MeOH elutions was further resolved by HPLC eluted with 10% THF in MeOH-hexane gradients (5–15%). MeOH (0–1%) in the mixture of hexane and EtOAc (2:1) and acetone in CHCl$_3$ (0–10%) to yield acetogenins (1–2).

Bullatin (1)

Compound (1) was obtained as a colorless wax (12.5 mg). [α]D+7.5° (c=0.4 mg/ml, EtOH). Uv $\lambda_{max}$EtOH nm:213 (log e=2.34). Ir $V_{max}^{film}$cm$^{-1}$:3442(OH), 2971, 2849, 1748 (C=O), 1458, 1186, 1051. FAB HR-MS (glycerol) m/z:623.4865 ([M+H])$^+$, found), (required 623.4887, Calcd. for $C_{37}H_{66}O_7$). EIMS, EIMS (triTMSi derivative), and EIMS (tri-d$_9$-TMSi derivative) m/z see Table 2. $^1$H NMR (500 MHz, CDCl$_3$); see Table 1. $^{13}$C NMR (125.75 MHz, CDCl$_3$); see Table 1.

Bullatin Triacetate (1a)

Treatment of compound (1) (2 mg) with Ac$_2$O-pyridine (at room temperature, overnight) and subsequent workup gave 1a as a colorless wax. $^1$H NMR (500 MHz, CDCl$_3$); see Table 1.

Bullanin (2)

Compound (2) was obtained as a colorless wax (10 mg). [α]D+28° (c=0.5 mg/ml, EtOH). Uv $\lambda_{max}$EtOH nm:220 (log e=2.42). Ir $\gamma_{max}^{film}$cm$^{-1}$: 3442 (OH), 2927, 2852, 1747 (C=O), 1459, 1320, 1193, 1070. FAB HRms (glycerol) m/z:623.4915 ([M+H]$^+$, found), (623.4887, Calcd. for $C_{37}H_{66}O_7$). EIMS, EIMS (triTMSi derivative), and EIMS (tri-d$_9$-TMSi derivative) m/z see Table 4. $^1$H NMR (500 MHz, CDCl$_3$); see Table 3. $^{13}$C NMR (125.75 MHz, CDCl$_3$); see Table 3.

Bullanin triacetate (2a)

Treatment of compound (2) (2 mg) with Ac$_2$O-pyridine (at room temperature, overnight) and subsequent workup gave 2a as a colorless was. $^1$H NMR (500 MHz, CDCl$_3$); see Table 3.

Asimicin was the first acetogenin isolated from the seeds and stem bark of the North American paw paw tree, *Asimina triloba* Dunal (Annonaceae). Asimicin has been reported as exhibiting highly potent antitumor and pesticidal activities. Further studies of *A. triloba* stem bark has led to the discovery of additional novel bioactive acetogenins, including the very active adjacent bis-tetrahydrofuran (THF) compound, trilobacin. The absolute stereochemistry of asimicin has now been defined, and the mechanism of action of asimicin and other Annonaceous acetogenins is via inhibition of NADH: ubiquinone oxidoreductase (complex I) in mitochondrial electron transport systems.

Further activity-directed fractionation of the ethanolic extract of the stem bark, using the brine shrimp lethality test (BST) to monitor fractionation, has revealed three novel adjacent bis-THF acetogenins, asimin (3), asiminacin (4) and asiminecin (5). Compounds 3–5 are structurally identified as asimicin isomers with the C-4 hydroxyl group moved to the C-10, C-28 and C-29 positions, respectively. These three compounds are nearly identical in their $^1$H- and $^{13}$C-NMR spectra. The determinations of the hydroxyl group positions were based on the mass spectral analysis of their tri-TMSi and tri-d$_9$-TMSi derivatives. Cell culture data showed these compounds have highly potent in vitro cytotoxicities against three human tumor cell lines in cytotoxicity tests.

EXAMPLE 3

Isolation of asimin, asiminacin and asiminecin

In searching for new bioactive acetogenins from the F005 fraction, which was partitioned from the EtOH extract of the stem bark, the more polar column fractions from the most active pools (P7–P9) were investigated. The fraction sample was subjected to open column and chromatotron chromatography with gradient elutions using MeOH and $CH_2Cl_2$ and 0–5% of MeOH in a mixture of CHCl$_3$ and hexane (2:3). Fractions 14–19 on TLC plates exhibited a unique spot which failed to be further resolved on additional chromatotron plates. At first this material was considered as a single compound. The $^1$H-NMR spectrum appeared to represent a single compound, but expansion of the proton signals of the terminal methyl groups showed an overlap of several compounds. A satisfactory separation was then achieved by

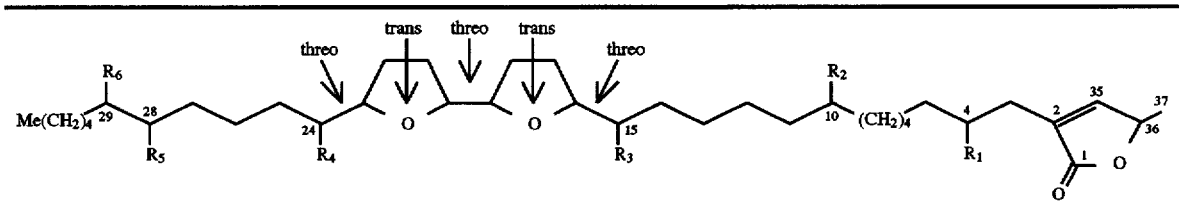

| Compounds | R₁ | R₂ | R₃ | R₄ | R₅ | R₆ |
|---|---|---|---|---|---|---|
| Asimicin | OH | H | OH | OH | H | H |
| Asimin (3) | H | OH | OH | OH | H | H |
| Asimin triacetate (3a) | H | OAc | OAc | OAc | H | H |
| Asiminacin (4) | H | H | OH | OH | OH | H |
| Aciminacin triacetate (4a) | H | H | OAc | OAc | OAc | H |
| Asiminecin (5) | H | H | OH | OH | H | OH |
| Asiminecin triacetate (5a) | H | H | OAc | OAc | H | OAc | using HPLC. Four separated HPLC peaks (AD) were obtained by using 8 μm normal phase silica gel HPLC columns with gradient elution of 8–12% of a mixture of MeOH and tetrahydrofuran (9:1) in hexane. Peak C was in pure form and gave compound 5. Further resolution of peak A was satisfactorily achieved to give compounds 3 and 4 in pure form by decreasing the MeOH percentage to 5–10% and increasing the ramping time.

Compound 3 was obtained as a colorless wax. A CIMS (isobutane) peak at m/z 623 indicated the molecular weight of 622. HR FABMS (glycerol) found the molecular ion peak at m/z 623.4907 which closely matched the exact mass 623.4887 calculated for the molecular formula $C_{37}H_{66}O_7$. An IR absorption band at 1751.6 cm$^{-1}$ and UV $\lambda_{max}$ at 215 nm and the $^1$H-NMR spectrum peaks (Table 6) at 66.99 (q, H-35), 5.00 (qq, H-36), as well as $^{13}$C-NMR resonances (Table 6) at δ173.80 (C-1) 134.20 (C-2), 148.82 (C-35), 77.41 (C-36), 19.27 (C-37), and 25.20 (C-3), suggested the presence of an α,β-unsaturated λ-lactone ring as previously reported in trilobacin and asimicin. Spectral comparisons of compound 3 and asimicin clearly indicated that the H-35 and H-36 proton signals and the C-35 and C-36 carbon resonances of 3 were shifted slightly upfield and the C-1 and C-2 signals were shifted downfield; the H-3a and N-3b peaks, characteristic in the $^1$H-NMR spectrum of asimicin were missing in 3, and the appearance of a multiplet peak at δ2.26 (tt, 2H) suggested the absence of a hydroxyl group at the C-4 position. Therefore, the presence of the typical subunit, fragment A, was substantiated.

The integrations for four protons in the multiplet signal at 3.85 ppm (H-16, 19, 20, and 23) and for two protons in the broad peak at 3.40 ppm (H-15 and 24), in the $^1$H-NMR spectrum (Table 6) of 3, indicated that 3 is an adjacent bis-THF-acetogenin. The $^{13}$C-NMR spectrum (Table 6), likewise, showed three pairs of closely located

TABLE 6

NMR Data for Asimin (3) and Its Triacetate derivative (3a)

| H/C No. | $^1$H-NMR (500 MHz, CDCl₃, δ in ppm, J in Hz) | | $^{13}$C-NMR (125.75 MHz, CDCl₃, δ in ppm) |
|---|---|---|---|
| | 3 | 3a | |
| 1 | — | — | 173.80 |
| 2 | — | — | 134.20 |
| 3 | 2.26 tt (7.8, 1.6) | 2.26 tt (7.8, 1.6) | 31.94–22.73 |

TABLE 6-continued

NMR Data for Asimin (3) and Its Triacetate derivative (3a)

| H/C No. | $^1$H-NMR (500 MHz, CDCl₃, δ in ppm, J in Hz) | | $^{13}$C-NMR (125.75 MHz, CDCl₃, δ in ppm) |
|---|---|---|---|
| | 3 | 3a | |
| 9, 11 | 1.44 m | 1.46–1.64 m | 37.43, 37.45 |
| 10 | 3.59 m | 4.86 m | 71.84 |
| 14, 25 | 1.65 m | 1.46–1.64 m | 33.39, 33.46 |
| 15, 24 | 3.40 m | 4.86 m | 73.97, 74.08 |
| 16, 23 | 3.85 m | 3.99 m | 83.05, 83.17 |
| 17a, 18a, 21a, 22a | 1.98 m | 1.95 m | 31.94–22.73 |
| 17b, 18b, 21b, 22b | 1.65 m | 1.78 m | 31.94–22.73 |
| 19, 20 | 3.85 m | 3.91 m | 81.76 81.81 |
| 4–8, 12–13, 26–33 | 1.24–1.60 m | 1.20–1.38 m | 31.94, 29.66, 29.64, 29.57, 29.37, 29.30, 29.14, 29.03, 29.02, 28.39, 27.41, 25.73, 25.70, 25.64, 25.20 22.73 |
| 34 | 0.878 t (7.0) | 0.879 t (7.0) | 14.18 |
| 35 | 6.99 q (1.5) | 6.99 q (1.5) | 148.82 |
| 36 | 5.00 qq (6.8, 1.7) | 5.00 qq (6.8, 1.7) | 77.41 |
| 37 | 1.41 d (6.5) | 1.41 d (7.0) | 19.27 |
| 15-OAc | | 2.08 s | |
| 24-OAc | | 2.08 s | |
| 10-OAc | | 2.04 s | | resonance peaks, at δ83.05 and 83.17, 81.76 and 81.81, and 73.97 and 74.08, which confirmed the presence of a moiety having adjacent bis-THF rings with two flanking hydroxyl groups. These proton and carbon signals were very similar to those observed with asimicin. In order to determine the relative stereochemistry between the adjacent chiral centers in this fragment, a triacetate derivative (3a) was made. The $^1$H-NMR data of 3a (Table 6) showed three separated oxygen-bearing methine signals; two of these peaks were integrated for two protons each at the resonances of δ3.91 and 3.99 arising from H-19, 20 and H-16, 23, respectively; the third signal, which integrated for three oxygen-bearing methine protons, was located at δ4.86 and had shifted downfield due to the acetylation of three hydroxyl groups; two of the hydroxyls were those flanking both sides of the bis-THF ring system. This chemical shift pattern closely matched the relative stereochemistry of a threo-trans-threo-trans-threo system which is identical to that of asimicin and is represented by fragment B. A slight separation of the three pairs of oxygen-related carbons hinted the influence of the third hydroxyl group located near the bis-THF ring system.

The presence of the three hydroxyl groups in 3 was confirmed by the IR absorption at 1751.6 cm−1 and the proton signals at δ3.40 (2H) and 3.59 (¹H). In the CIMS spectrum (Table 7), the observation of a series of fragments at m/z 605,587, and 569, due to successive losses of three molecules of water, further confirmed the presence of three hydroxyl groups. Additional evidence was provided by the three acetate methyl signals at δ2.04 (3H) and 2.08 (6H) in the ¹H-NMR spectrum of 3a and the fragment peaks at m/z 689, 629, and 569 arising from the successive losses of three acetates (m/z 60) from the molecular ion at m/z 749 in the CIMS spectrum of 3a. Two hydroxyl groups were those flanking the THF ring, and the third hydroxyl, which exhibited its methine proton signal at δ3.59 and its carbon resonance at δ71.84, was predicted to be nearby in the aliphatic chain.

Having determined the presence of fragments A and B and the three hydroxyl groups, the remaining portions of the structure of compound 3 consisted simply of two aliphatic chains. To establish the location of these fragments and hydroxyl groups along the aliphatic chains, the triTMSi and tri-d₉-TMSi derivatives were prepared. Analysis of the EIMS spectra (Table 7) of these derivatives determined that the adjacent bis-THF ring system was located at C-16 to C-23 and the three hydroxyl groups are at C-10, C-15 and C-24. Thus, the structure of compound 3 was established as that illustrated above, and 3 was given the name of asimin.

Compound 4 was isolated as a wax in a similar amount as 3. The CIMS (isobutane) spectrum (Table 8) of 4 showed a [M+H]⁺ ion at m/z 623, indicating a molecular weight of 622, identical to the molecular weight of 3. The HR FABMS (glycerol) gave a peak for the molecular ion at m/z 623.4874 corresponding to the calculated exact mass of 623.4887 for the molecular formula $C_{37}H_{66}O_7$.

As determined with 3, the presence of a terminal α,β-unsaturated λ-lactone ring, without a 4—OH group (fragment A), and an adjacent bis-THF ring moiety (fragment B) was obvious from the ¹H- and ¹³C-NMR spectra of 4 (Table 9) and by NMR spectral comparisons with compound 3. The presence of three OH groups was also recognized by the analysis of IR, ¹H-NMR, ¹³C-NMR, and CIMS spectra of 4 and the CIMS spectrum of its triacetate derivative (4a). The related stereochemistry in the bis-THF ring moiety was also established as a threo-trans-threo-trans-threo system based on the ¹H-NMR spectral analysis of 4a.

The placements of the adjacent bis-THF ring system (fragment B) and the three hydroxyl groups of 4 along the

TABLE 7

| R | M+/MH+ | A | B | C | D | E | F | G |
|---|---|---|---|---|---|---|---|---|
| H (CIMS) | 623 | | 225 | 311 (a) | | 241* | | 171 |
| | 605 (a) | | | 293 (a) | | 223* (a) | | |
| | 587 (a) | | | 275 (a) | | | | |
| | 569 (a) | | | | | | | |
| TMS (EIMS) | 838* | 643 | 297 | 455 | | 313* | 595 | 243 |
| | 748 (b) | 553 (b) | 207* (b) | 365 (b) | | 223* (c) | 505 (b) | 153* (b) |
| | 658* (b) | 463* (b) | | 275* (b) | | | 415 (b) | |
| | 568* (b) | 273* (b) | | | | | | |
| D₉-TMS (EIMS) | 865* | 670 | 306 | 473 | 543 | 322* | 613 | 252 |
| | 766 (c) | 571 (c) | 207* (c) | 374 (c) | 444 (c) | 223* (c) | 514 (c) | 153* (c) |
| | 667 (c) | 472 (c) | | 275 (c) | 345 (c) | | 415 (c) | |
| | 568 (c) | 373* (c) | | | | | | |

(a): loss of H₂O (m/z 18); (b): loss of TMSi (m/z 90); (c): loss of d₉-TMSi (m/z 99); *weak intensity.
Diagnostic mass fragmentation ions of asimin (3) and its triTMSi and tri-d₉-TMSi derivatives.

TABLE 8

Diagnostic mass fragmentation ions of asiminacin (4) and its triTMSi and tri-d₉-TMSi derivatives.

| R | M+/MH+ | A | B | C | D | E | F | G | H | I |
|---|---|---|---|---|---|---|---|---|---|---|
| H (CIMS) | 623<br>605 (a)<br>587 (a)<br>569 (a) | 295<br>277* (a) | 327*<br>309 (a) | 365*<br>347 (a) | 257<br>239 (a) | 435* | | | 115* | |
| TMS (EIMS) | 838*<br>748 (b)<br>658* (b)<br>568* (b) | 367<br>277* (b) | 471<br>381* (b)<br>291 (b) | 437<br>347 (b) | | 507<br>417 (b) | 331<br>241 (b)<br>151* (b) | | 187 | 753<br>663 (b)<br>573* (b)<br>483* (b) |
| d₉-TMS (EIMS) | 865*<br>766 (c)<br>667 (c)<br>568 (c) | 376 | 489<br>390* (c)<br>291 (c) | 446<br>347 (c) | | 516<br>417 (c) | 349<br>250 (c)<br>151* (c) | 669<br>570 (c)<br>471* (c) | 196 | 780* |

(a): loss of H₂O (m/z 18); (b): loss of TMSi (m/z 90); (c): loss of d₉-TMSi (m/z 99); *weak intensity.

TABLE 9

NMR Data for Asiminacin (4) and Its Triacetate derivative (4a)

| H/C No. | ¹H-NMR (500 MHz, CDCl₃, δ in ppm, J in Hz) 4 | ¹H-NMR 4a | ¹³C-NMR (125.75 MHz, CDCl₃, δ in ppm) |
|---|---|---|---|
| 1 | — | — | 173.83 |
| 2 | — | — | 134.25 |
| 3 | 2.26 tt (7.8, 1.6) | 2.26 tt (7.8, 1.6) | 31.88–22.67 |
| 14, 25 | 1.67 m | 1.46–1.64 m | 33.45, 33, 22 |
| 15, 24 | 3.40 m | 4.85 m | 73.89, 74.07 |
| 16, 23 | 3.86 m | 3.98 m | 83.05, 83.19 |
| 17a, 18a, 21a, 22a | 1.98 m | 1.95 m | 31.88–22.67 |
| 17b, 18b, 21b, 22b | 1.67 m | 1.79 m | 31.88–22.67 |
| 19, 20 | 3.86 m | 3.90 m | 81.78, 81.85 |
| 27, 29 | 1.44 m | 1.46–1.64 m | 37.31, 37.56 |
| 28 | 3.60 m | 4.85 m | 71.73 |
| 4–13, 26, 30–33 | 1.22–1.72 m | 1.20–1.38 m | 31.88, 29.64, 29.55, 29.41, 29.34, 29.22, 29.04, 29.00, 28.40, 27.42, 25.71, 25.69, 25.21, 21.78, 22.67 |
| 34 | 0.882 t (7.0) | 0.876 t (7.0) | 14.15 |
| 35 | 6.99 q (1.5) | 6.99 q (1.5) | 148.78 |
| 36 | 5.00 qq (6.8, 1.7) | 5.00 qq (6.8, 1.7) | 77.40 |
| 37 | 1.41 d (6.5) | 1.41 d (7.0) | 19.27 |
| 15-OAc | | 2.08 s | |
| 24-OAc | | 2.08 s | |
| 28-OAc | | 2.03 s | | aliphatic chain were determined based on the fragmentation pattern of the triTMSi and tri-d₉-TMSi derivatives of 4 in their EIMS spectra (Table 8). That the bis-THF ring was located from C-16 to C-23, and the three hydroxyl groups were situated at the C-15, C-24 and C-28 positions. Hence, the only difference between 3 and 4 is that the third hydroxyl group is positioned at C-10 in compound 3, while compound 4 has its third hydroxyl group at C-28. Compound 4 was given the trivial name asiminacin.

Compound 5 is another waxy compound. A molecular ion peak at m/z 623 in the CIMS (isobutane) spectrum of 5 (Table 10), indicated a molecular weight of 622. The HR CIMS (isobutane) spectrum showed an exact mass peak at m/z 623.4868 which matched the molecular formula $C_{37}H_{66}O_7$ (calculated 623.4887).

The IR, UV, ¹H-NMR, ¹³C-NMR spectra of 5 (Table 11) were very similar to those of 3 and 4. Comparisons of these spectra gave the indication that 5 could also possess the identical structural skeleton as that of asimin (3) and asiminacin (4); this included the terminal α,β-unsaturated lactone ring (fragment A), the adjacent bis-THF ring system (fragment B), and three hydroxyl groups. The related stereochemistry in the bis-THF ring system was defined as having the threo-trans-threo-trans-threo pattern by the analysis of the usual diagnostic proton chemical shifts in the ¹H -NMR spectrum of the triacetate 5a.

The EIMS diagnostic fragment peaks of the triTMSi and tri-d₉-TMSi derivatives of 5 (Table 10) determined the location of the adjacent bis-THF ring system at C-16 to C-23 and the two flanking hydroxyl groups at C-15 and C-24 which were identical to the structures of 3 and 4. The placement of the third hydroxyl group at C-29 was suggested by fragment ions at m/z 173 and 767 in the EIMS spectrum of the triTMSi derivative of 5 and was confirmed by the corresponding diagnostic ions at m/z 182 and 794 in the

TABLE 10

Diagnostic mass fragmentation ions of asiminecin (5) and its triTMSi and tri-d₉-TMSi derivatives.

| R | M+/MH+ | A | B | C | D | E | F | G |
|---|---|---|---|---|---|---|---|---|
| H | 623 | 295 | 365 | 257* | 435* | | | 551 |
| (CIMS) | 605 (a) | 277* (a) | 347 (a) | 239 (a) | 417 (a) | | | |
| | 587 (a) | | | | | | | |
| | 569 (a) | | | | | | | |
| TMS | 838* | 367 | 437 | 401* | 507 | 331 | 173 | 767 |
| (EIMS) | 748 (b) | | 347 (b) | 311 (b) | 417 (b) | 241* (b) | | |
| | 658* (b) | | | | | 151* (b) | | |
| | 568* (b) | | | | | | | |
| D₉-TMS | 865* | 376 | 446 | 419* | 516 | 349* | 182 | 794 |
| (EIMS) | 766 (c) | | 347 (c) | | 417 (c) | 250 (c) | | (695) |
| | 667 (c) | | | | | 151 (c) | | (596) |
| | 568 (c) | | | | | | | 497 (c) |

(a): loss of $H_2O$ (m/z 18); (b): loss of TMSi (m/z 90); (c): loss of d₉-TMSi (m/z 99); *weak intensity.

TABLE 11

NMR Data for Asiminecin (5) and Its Triacetate derivative (5a)

| H/C No. | ¹H-NMR (500 MHz, CDCl₃, δ in ppm, J in Hz) 5 | 5a | ¹³C-NMR (125.75 MHz, CDCl₃, δ in ppm) |
|---|---|---|---|
| 1 | — | — | 173.83 |
| 2 | — | — | 134.25 |
| 3 | 2.26 tt (7.8, 1.6) | 2.26 tt (7.8, 1.6) | 31.94–22.69 |
| 14, 25 | 1.68 m | 1.46–1.64 m | 33.47, 33.33 |
| 15, 24 | 3.40 m | 4.85 m | 74.07, 73.87 |
| 16, 23 | 3.86 m | 3.98 m | 83.17, 83.05 |
| 17a, 18a, 21a, 22a | 1.98 m | 1.95 m | 31.94–22.69 |
| 17b, 18b, 21b, 22b | 1.68 m | 1.78 m | 31.94–22.69 |
| 19, 20 | 3.86 m | 3.90 m | 81.82, 81.78 |
| 28, 30 | 1.44 m | 1.46–1.64 m | 37.52, 37.33 |
| 29 | 3.60 | 4.85 | 71.81 |
| 4–13, 26–27, 31–33 | 1.22–1.72 m | 1.20–1.38 m | 31.94, 29.63, 29.54, 29.34, 29.21, 29.03, 29.02, 28.41, 28.3927.42, 25.70, 25.61, 25.58, 25.38, 22.69 |
| 34 | 0.891 t (7.0) | 0.880 t (7.0) | 14.11 |
| 35 | 6.99 q (1.5) | 6.99 q (1.5) | 148.79 |
| 36 | 5.00 qq (6.8, 1.7) | 5.00 qq (6.8, 1.7) | 77.41 |
| 37 | 1.41 d (7.0) | 1.41 d (7.0) | 19.26 |
| 15-OAc | | 2.08 s | |
| 24-OAc | | 2.08 s | |
| 29-OAc | | 2.04 s | |

EIMS spectrum of the tri-d₉-TMSi derivative of 5. Isolate 5 was given the trivial name asiminecin.

The three novel acetogenins (3–5) are very toxic in the brine shrimp test (BST). This test continues to be a convenient bench-top procedure to discover new cytotoxic compounds. Bioactivity data of compounds 3–5, against three human tumor cell lines, are presented in Table 5. In all cytotoxicity experiments performed human solid tumor cytotoxicity values are determined in the same run to eliminate possible variations. Values for adriamycin, as a positive control in the same run, are also presented for comparison. In the cytotoxicity experiments conducted by Applicants at the Purdue Cancer Center, 3–5 showed extremely potent cytotoxicities against A-549 (lung cancer), MCF-7 (breast cancer) and H-29 (colon cancer) cell lines. Compounds 3–5 exhibited high selectivity against H-29 cancer cells with $ED_{50}$ values as low as $10^{-12}$ µg/ml. The overall activities of these three compounds (3–5) are equally or more active than the previously reported compounds trilobacin, asimicin and bullatacin and much more active than 4-deoxyasimicin (5) which lacks a third hydroxyl. It appears that the substitution of the third hydroxyl group greatly enhances the cytotoxic activity. When the third hydroxyl group is substituted at the C-10, C-28 or C-29 positions, the substitution is equally or more effective in enhancing the cytotoxic activity of the compound as a substitution at the C-4 position.

Experimental Details for Isolation and Characterization of Compounds 3, 4 and 5.

Instrumentation. Mp determinations were made on a Mel-Temp apparatus and are unconnected. Optical rotations were taken on a Perkin Elmer 241 polarimeter. IR spectra were obtained on a Perkin-Elmer 1600 FTIR spectrometer. UV spectra were measured on a Beckman DU-7 UV spectrometer. ¹H and ¹³C NMR spectra were recorded on a Varian VXR-500S (¹H at 500 MHz, ¹³C at 125.75 MHz) spectrometer in CDCl3 with resonance signals referenced to TMS. Low resolution CIMS, EIMS and FAB MS data were collected on a Finnigan 4000 spectrometer. EIMS for TMSi and d₉-TMSi derivatives and exact mass measurements through peak matching were performed on a Kratos MSSO mass spectrometer. TLC separations were made on Si gel 60 F-254 (EM57 17) glass plates (0.25 mm) and visualized by spraying with 5% phosphomolybdic acid in EtOH and heating. Chromatotron plates (1 or 2 mm) were prepared with silica gel 60 PF 254 containing gypsum and dried at 700 overnight. HPLC was carried out with a Rainin HPLC instrument using the Dynamax software system and a silica gel column (250×21 mm) equipped with a Rainin UV-1 detector set at 220 nm. Chemicals. For preparation of triTMSi and tri-d9-TMSi derivatives, N, O-bis-(trimethylsilyl)-acetamide (BSA) and pyridine in silylation grade were purchased from Pierce Chemical Company (USA); d18-bis-(trimethylsilyl)trifluoroacetamide (d18-BSTFA) was from Regis Chemical Company (USA) under the brand name Deutero Regis-d 18.

Derivatization. TriTMSi and tri-$d_9$-TMSi derivatives were prepared by treatment of the isolated acetogenins with BSA for the triTMSi derivatives or $d_{18}$-BSTFA for the tri-$d_9$-TMSi derivatives in the presence of pyridine. Approximately 10–50 μg of pure compound was placed in a 100 μl conical reaction vial and dried in a vacuum desiccator over $P_2O_5$ for 24 hrs. The sample was treated with 2 μl pyridine and 20 μl of BSA or $d^{18}$-BSTFA and heated at 70° C. for 30 min. The EIMS measurements of the derivatives were carried out at a resolution of 1500, scanning mass 900–100 at 30 sec./decade.

Bioassays. The brine shrimp (*Artemia salina* leach) test (BST) was performed as modified. Zhao et al., *Phytochemistry*, 33, p. 1065 (1993). Seven-day in vitro cytotoxicity tests against human tumor cell lines were carried out at the Purdue Cancer Center, using standard protocols for A-549 (human lung carcinoma), Gu, Z.-M.; Fang, X.-P.; Miesbauer, L. R., Smith, D. L.; and McLaughlin, J. L., 30, 31, and 32-Hydroxybullatacinones: Bioactive Terminally-Hydroxylated Annonaceous Acetogenins from *Annona bullata*., *J. Nat. Prod.*, 1993, 56, 870–876; MCF-7 (human breast carcinoma) McLaughlin, J. L., Chang, C.-J., and Smith, D. L., Simple Bench-Top Bioassays (Brine Shrimp and Potato Discs) for the Discoveries of Plant Antitumor Compounds: A Review of Recent Progress. In Kinghorn, A. D., Blanadrin, J. (Eds): "Human Medicinal Agents from Plats", ACS Symposium Series, Washington, D.C., American Chemical Society, 1993, pp. 112–137; and HT-29 (human colon carcinoma), Mclaughlin, J. L., Chang, C.-J., Smith, D. L., "'Bench-Top' Bioassays for the Discovery of Bioactive Natural Products: An Update", in Rahman, Atta-ur- (Ed): "Studies in Natural Product Chemistry", Vol. 9, Amsterdam, Elsevier, 1991, pp. 383–409, with adriamycin as a positive control. The reported values (Table IV) were tabulated from the same run in order to facilitate comparison for the SAR's.

Plant materials for Compounds 3–5. The bark of *Asimino triloba* (L.) Dunal was collected from stands growing wild at the Purdue Horticultural Research Farm. The identification was confirmed by Dr. George R. Parker, Department of Forestry and Natural Resources, Purdue University. A voucher specimen of the bark is preserved in the pharmacognosy herbarium.

Extraction and purification. The air-dried pulverized stem bark (15 kg) was extracted exhaustively with 95% EtOH and vacuum evaporated to yield extract F001 (1645 g) which was partitioned between $H_2O$ and $CH_2Cl_2$ (1:1), giving a water soluble fraction (F002, 5 g), $CH_2Cl_2$ soluble fraction (F003, 1560 g) and an insoluble interface (F004, 80 g). F003 was further partitioned between hexane and 90% MeOH aqueous solution and yielded the MeOH fraction (F005, 650 g) and the hexane fraction (F006, 905 g).

Directed by the BST bioassay, the most bioactive fraction, F005 (BST $LC_{50}$ 7.151×10$^{-1}$ μg/ml) (200 g) was further fractionated by open column chromatography on silica gel (8 Kg, 60–200 mesh), eluting with hexane-EtOAc and EtOAc-MeOH gradients; 12 pools were made from the collected fractions according to their TLC patterns and evaluated by the BST bioassay. The most active pools ($P_7$–$P_9$) were combined (20 g) and subjected to further repeated separation by silica gel (1000 g, 230–400 mesh) column chromatography eluted with MeOH—$CHCl_3$ gradients. Further purifications of the most bioactive fractions F11–12 (1.2 g, BST $LC_{50}$ 3.5×10$_{-2}$ mg/ml) were carried out on Chromatotron plates (2 mm thick), eluted with hexane-$CH_2Cl_2$—MeOH (30:20:0–5). The white wax from the hexane-$CH_2Cl_2$—MeOH fractions was further resolved by HPLC eluted with 10% THF in MeOH-hexane gradients to yield the new acetogenins 3–5.

Asimin (3). Colorless wax (12 mg), [α]D+26 ($CHCl_3$, 1 mg/ml). UV $\lambda_{max}$ MeOH nm: 215. IR $V_{max}$ film cm$^{-1}$: 3437.9 (OH), 2925.1, 2855.3, 1751.6 (C=O), 1457.4, 1318.3, 1199.6, 1068.8, 954.0, 870.1. FAB HR-MS (glycerol) m/z: 623.4907 ([M+H]$^+$, found), (623.4887, calcd. for $C_{37}H_{66}O_7$). CIMS m/z: see Figure II. EIMS (triTMSi derivative) m/z. EIMS (tri-$d_9$-TMSi derivative) m/z: see Figure II. $^1$H-NMR (500 MHz, $CDCl_3$): see Table 6. $^{13}$C-NMR (125.75 MHz, $CDCl_3$): see Table 1.

Asimin triacetate (3a). Treatment of 3 (4 mg) with $Ac_2O$-pyridine (at room temperature, overnight) and subsequent workup gave 3a as a wax. IR $V_{max}$ film cm$^{-1}$: 2926, 2855, 1758, 1733, 1459, 1368, 1317, 1241, 1068, 1022, 951. CIMS (isobutane) m/z 749 [M+H]+, 689 [MH—$CH_3COOH$]+, 629 [MH—$2CH_3COOH$]+, 569 [MH—$3CH_3COOH$]+, 551, 517, 465, 421, 405, 345, 327, 219. $^1$H-NMR (500 MHz, $CDCl_3$): see Table 6.

Asiminacin (4). Colorless wax (12 mg), [α]D+21.1 ($CHCl_3$, 3.8 mg/ml). UV $\lambda_{max}$ MeOH nm: 215. IR $V_{max}$ film cm$^{-1}$: 3418.1 (OH), 2925.0, 2855.9 1752.8 (C=O), 1456.7, 1318.6, 1199.5, 1068.9, 953.0, 872.2. FAB HR-MS (glycerol) m/z: 623.4874 ([M+H]+, found), (623.4887, calcd. for $C_{37}H_{66}O_7$). CIMS m/z: see Table 8. EIMS (triTMSi derivative) m/z see Table 8. EIMS (tri-$d_9$-TMSi derivative) m/z see Figure III. $^1$H-NMR (500 MHz, CDCl3): see Table 9. $^{13}$C-NMR (125.75 MHz, $CDCl_3$): see Table 9.

Asiminacin triacetate (4a). Treatment of 4 (4 mg) with $Ac_2O$-pyridine (at room temperature overnight) and subsequent workup gave 4a as a wax. IR $V_{max}$ film cm$^{-1}$: 2929, 2855, 1753, 1732, 1456, 1369, 1317, 1241, 1072, 1020, 949. CIMS (isobutane) m/z 749 [M+H]+, 689 [MHCH$_3$COOH] +629 [MH—$2CH_3COOH$]+, 569 [MH—$3CH_3COOH$]+, 551, 465, 423, 407, 351, 347, 329, 219. $^1$H-NMR (500 MHz, $CDCl_3$): see Table 9.

Asiminecin (5). Colorless wax (10 mg), [α]D+22 ($CHCl_3$, 1 mg/ml). UV $\lambda_{max}$ MeOH nm: 215. IR $V_{max}$ film cm$^{-1}$: 3419.4 (OH), 2925.0, 2855.9, 1751.3 (C=O), 1455.7, 1317.6, 1198.5, 1068.9, 953.0, 872.2. HR-CIMS (isobutane) m/z: 623.4868 ([M+H]$^+$, found), (623.4887, calcd. for $C_{37}H_{66}O_7$). CIMS m/z: see Table 10. EIMS (triTMSi derivative) m/z: see Table 10. EIMS (tri-$d_9$-TMSi derivative) m/z see Table 10. $^1$H-NMR (500 MHz, CDCl$_3$): see Table 11. $^{13}$C-NMR (125.75 MHz, $CDCl_3$): see Table 11.

Asiminecin triacetate (5a). Treatment of 5 (4 mg) with $Ac_2O$-pyridine (at room temperature, overnight) and subsequent workup gave 5 as a wax. IR $V_{max}$ film cm$^{-1}$: 2930, 2845, 1754, 1735, 1460, 1370, 1318, 1242, 1072, 1024, 953. CIMS (isobutane) m/z 749 [M+H]+, 689 [MHCH$_3$COOH]+, 629 [MH—$2CH_3COOH$]+, 569 [MH—$3CH_3COOH$]+, 521, 425, 397, 391, 369, 331, 295, 271, 257, 217, 201, 169, 101. $^1$H-NMR (500 MHz, $CDCl_3$): see Table 11.

*Goniothalamus giganteus* Hook. f. et Thomas (Annonaceae) is a tropical tree widely distributed in southeast Asia. Extracts of the bark, obtained from Thailand, showed toxicities in the brine shrimp test (BST) and showed murine toxicities in the 3PS (P388) leukemia bioassay. From the ethanol extract of the bark, eleven highly cytotoxic Annonaceous acetogenins have been isolated and, among them, four have a double bond in the aliphatic chain. The presence of a double bond is a relatively rare feature in the Annonaceous acetogenins. Over 90 acetogenins have been described, yet, only one additional acetogenin, bullatenin from *Annona bullata*, has been found having a double bond in the chain. We have isolated from the bark of *G. giganteus* a new mono-THF acetogenin, gonionenin, which also has a double bond in the aliphatic chain. The C-21/22 double acetogenins through epoxidation and cyclization from mono-THF acetogenins possessing a chain double bond.

Gigantetronenin (28) is a major acetogenin isolated from *G. giganteus* and contains a mono-THF and an isolated chain double bond. Recently, 28 was also found in *Xylopia*

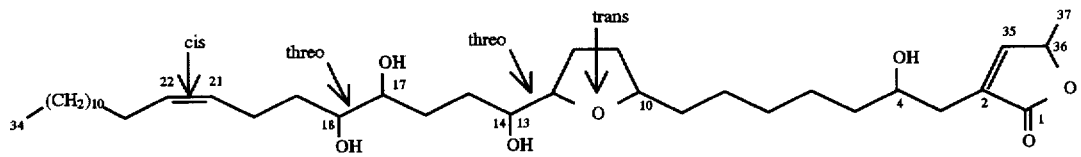

(28) Gigantetronenin

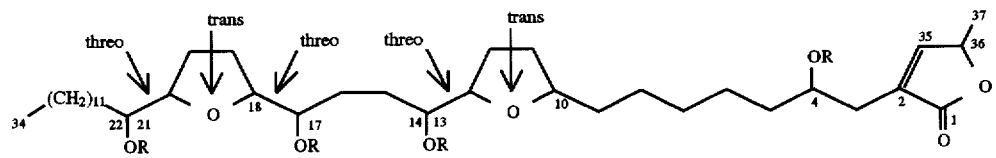

(29) Gigantecin, R = H,
(32) Gigantecin Tetraacetate, R = Ac
(33) Tetra-TMS Derivative of Gigantecin, R = TMS

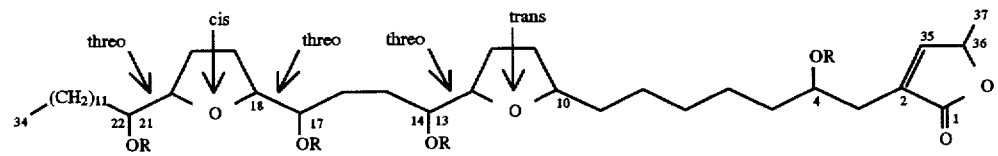

(22) C-18/21-cis-gigantecin, R = H
(30) C-18/21-cis-gigantecin Tetraacetate, R = Ac
(31) Tetra-TMS Derivative of C-18/21-cis-gigantecin, R = TMS

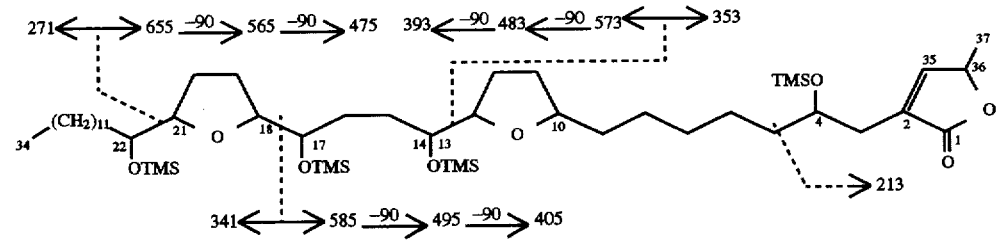

Compounds 22 and 29 bonds in gonionenin and another mono-THF acetogenin, gigantetronenin (28), previously isolated from this plant, were oxidized with m-chloroperbenzoic acid to epoxides which then were cyclized using perchloric acid with OH groups appropriately located to form another THF ring and give a pair of adjacent bis-THF and a pair of nonadjacent bis-THF (22 and 29) acetogenins, respectively. The reactions were facile and the yields of the products were high. This conversion of mono-THF acetogenins to adjacent or nonadjacent bis-THF acetogenins not only conclusively determined the position of the double bonds in the molecules, but also significantly increased the cytotoxic potencies against certain human solid tumor cell lines (Table 12). These reactions mimic proposed biogenetic pathways leading to the THF rings of Annonaceous acetogenins. This is the first reported preparation of bis-THF Annonaceous

TABLE 12

Bioactivities of compounds 28, 29, and 22.

| Comp | BST $LC_{50(\mu g/ml)}$ | A-549 $ED_{50(\mu g/ml)}$ | MCF-7 $ED_{50(\mu g/ml)}$ | HT-29 $ED_{50(\mu g/ml)}$ |
|---|---|---|---|---|
| 28 | 10.4 | $2.22 \times 10^{-8}$ | $1.49 \times 10^{-8}$ | $1.0 \times 10^{-12}$ |
| 29 | $3.44 \times 10^{-2}$ | $<10^{-12}$ | $1.0 \times 10^{-4}$ | $<10^{-12}$ |
| 22 | $2.49 \times 10^{-1}$ | $<10^{-12}$ | $<10^{-12}$ | $<10^{-12}$ |
| Adriamycin | $8 \times 10^{-2}$ | $9.20 \times 10^{-3}$ | $2.31 \times 10^{-1}$ | $3.92 \times 10^{-2}$ |

All the cytotoxicities against human tumor cell lines were tested in the same run; Adriamycin is included as a positive control standard
BST = Brine shrimp lethality test
A-549 = Human lung carcinoma
MCF-7 = Human breast carcinoma
HT-29 = Human colon adenocarcinoma

TABLE 13

| Comp | BST | A-549 | MCF-7 | HT-29 |
|---|---|---|---|---|
| 23 | 57 | $9.42 \times 10^{-1}$ | 4.85 | $1.61 \times 10^{-2}$ |
| Adriamycin | $8 \times 10^{-2}$ | $8.50 \times 10^{-3}$ | $5.19 \times 10^{-1}$ | $3.72 \times 10^{-2}$ |

All the cytotoxicities against human tumor cell lines were tested in the same run; Adriamycin is included as a positive control standard
BST = Brine shrimp lethality test
A-549 = Human lung carcinoma
MCF-7 = Human breast carcinoma
HT-29 = Human colon adenocarcinoma

*aromatica*. In a suggested biogenetic pathway of the acetogenins from *G. giganteus*, it has been suggested that 28 was possibly the precursor of gigantecin. To mimic this proposed biogenesis, 28 was treated with m-CPBA then perchloric acid and produced a mixture of 29 and 22 (Scheme I) which were separated by HPLC.

be as illustrated. The skeleton and relative stereochemistries of 29 were exactly the same as those of gigantecin, and co-TLC of 29 and gigantecin in several different solvent systems always showed them to be inseparable. Gigantecin, with low content, was isolated from *G. giganteus* previously by our group, was the first nonadjacent bis-THF acetogenin to be reported, and showed potent bioactivities in several bioassays. This conversion not only supports the hypothesis that gigantetronenin (28) may be the precursor of gigantecin (29) but also provides a new, more abundant, source of 29.

The carbon skeleton of 22, identical to that of 29, was determined by the EIMS analysis of the TMS derivative of 22. 22 differs from 29 only in the stereochemistry of

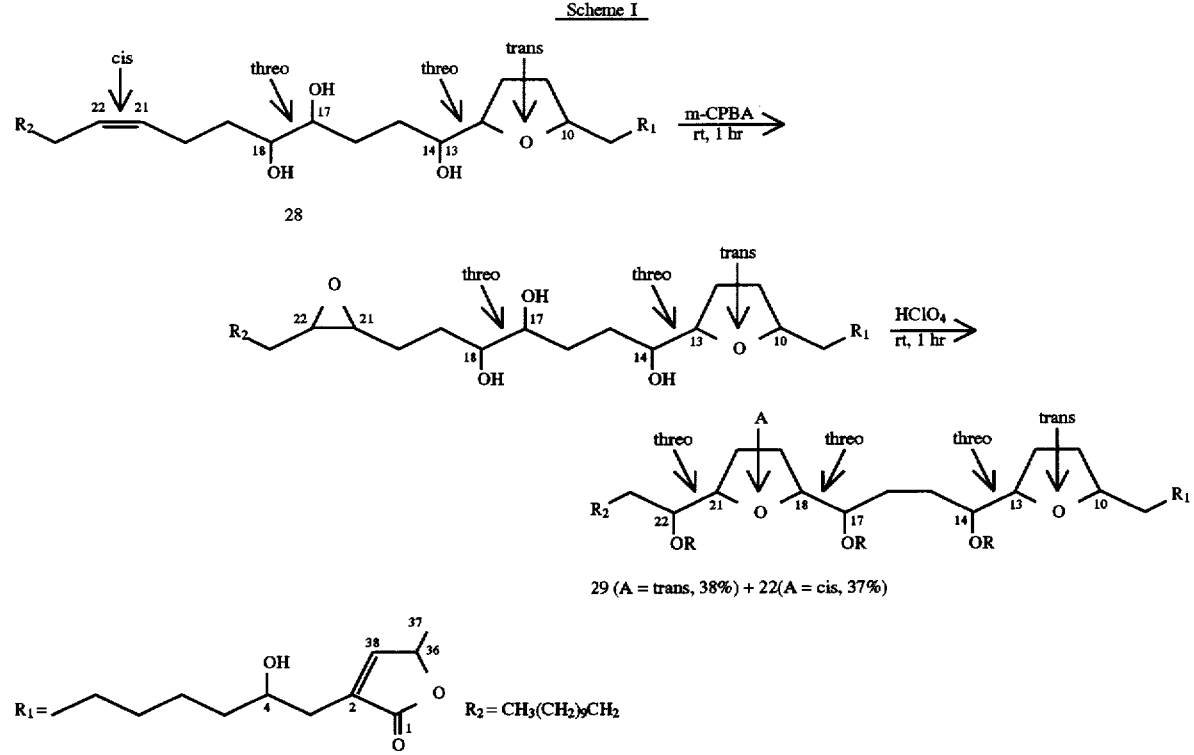

29 (A = trans, 38%) + 22(A = cis, 37%)

The disappearance of double bond NMR signals of 28, the proton signals at 83.83 (2H, H-18 and 21), 3.47 (H-17), and 3.40 (H-22), and carbon signals at δ82.8 (C-21), 82.7 (C-18), 74.3 (C-17 and 22) in 29 indicated the formation of a new THF ring, since both the $^1$H and $^{13}$C NMR data of the remainder of 29 were almost the same as those of 33. The carbon skeleton was confirmed by the EIMS analysis of the TMS derivative of 29. The proton signals of H-19a and 20a of this new THF were at δ1.98 and those of H-19b and 20b were at δ1.66; this suggested a trans arrangement for the THF (C- 18/21) and both of the carbon signals of the flanking hydroxyl-bearing carbons were at δ74.3 and indicated the threo configuration for both carbon centers C-17/18 and C-21/22. Thus, the structure of 29 was concluded to the newly formed THF ring (C-18/21). The proton signals of the THF methylene protons of 22 at δ1.94 and 1.78 (Table 14), instead of at δ1.98 and 1.65 corresponding to the trans THF arrangement, indicated the cis configuration for this THF ring. This result also matched well with the suggested mechanism of the cyclization; since 29 has the trans configuration for this THF, 22 should have the cis configuration. The structure of 22 (Scheme I), thus, was determined to be as illustrated; it represents a new type of nonadjacent bis-THF Annonaceous acetogenin and was named C- 18/21 -cis-gigantecin.

The bioassay data summarized in Table 12 indicates that the newly prepared bis-THF compounds are more bioactive than their parent compounds; the potent bioactivities of 29 and 22 are especially noteworthy and approach the levels previously observed with adjacent bis-THF acetogenins such as asimicin, trilobacin, and bullatacin.

27

Experimental Details for Isolation and Characterization of Compounds 22, 28 and 29.

Methods. Melting points were determined on a Mettler FP5 hot-stage apparatus and are uncorrected. Optical rotations were determinated on a Perkin Elmer 241 polarimeter. IR spectra (film) were measured on a Perkin-Elmer 1600 FTIR spectrometer. UV spectra were taken in MeOH on a Beckman DU-7 UV Spectrometer. $^1$H NMR, $^1$H—$^1$H COSY, and $^{13}$C NMR spectra were obtained on a Varian VXR-500S spectrometer. Low resolution MS data were collected on a Finnigan 4000 spectrometer. Low resolution EIMS for TMS derivatives was performed on a Kratos MS50. HRFABMS were measured on the Kratos MS50 spectrometer through peak matching. HPLC was performed with a Rainin HPLC using a Dynamax software system and a silica gel column (250×21 mm) equipped with a Rainin UV- 1 detector. Analytical TLC was performed on silica gel plates (0.25 mm) developed $^1$H NMR (500 MHz, CDCl$_3$) Data$^{a,b}$ of 29, 22 and 30 [δ ppm (J = Hz)]

| Proton | 29 | 22 | 30 |
|---|---|---|---|
| 3a | 2.53 ddd | 2.52 ddd | 2.56 ddd |
| 3b | 2.40 ddt | 2.40 ddt | 2.53 ddt |
| 4 | 3.84 m | 3.84 m | 5.10 m |
| 10 | 3.88 m | 3.88 m | 3.85 m |
| 11 | 2.02, 1.52 | 2.02, 1.50 | 1.97, 1.44 |
| 12 | 1.98, 1.66 | 1.98, 1.60 | 1.95, 1.54 |
| 13 | 3.80 m | 3.80 m | 3.95 m |
| 14 | 3.41 m | 3.42 m | 4.83 m |
| 15 | 1.72, 1.44 | 1.69, 1.48 | 1.57 m |
| 16 | 1.72, 1.44 | 1.72, 1.58 | 1.57 m |
| 17 | 3.41 m | 3.47 m | 4.86 m |
| 18 | 3.80 m | 3.83 m | 3.95 m |
| 19 | 1.98, 1.66 | 1.94, 1.78 | 1.90, 1.56 |
| 20 | 1.98, 1.66 | 1.94, 1.78 | 1.90, 1.56 |
| 21 | 3.80 m | 3.83 m | 3.95 m |
| 22 | 3.41 m | 3.40 m | 4.86 m |
| 23 | 1.44 m | 1.45 m | 1.39 m |
| 34 | 0.88 t (7) | 0.88 t (7) | 0.88 t (7) |
| 35 | 7.19 q (1.5) | 7.19 q (1.5) | 7.08 q (1.5) |
| 36 | 5.06 qq (7, 1.5) | 5.06 qq (7, 1.5) | 5.01 qq (7, 1.5) |
| 37 | 1.43 d (7) | 1.43 d (7) | 1.40 d (7) |
| 4-OAc | — | — | 2.02 s |
| 10/14-OAc | — | — | 2.07 s |
| 13/17-OAc | — | — | 2.08 s |
| 22-OAc | — | — | 2.09 s |

$^a$Assignments based on $^1$H-$^1$H COSY, single relayed COSY, and double relayed COSY in CDCl$_3$, TMS as the standard. $^b$Signals of other methylene protons appear between δ 1.70 and 1.21 m.

TABLE 15

$^{13}$C NMR (125 MHz, CDCl$_3$) Data 29 and 22

| C | 29$^a$ | 22$^b$ |
|---|---|---|
| 1 | 174.5 | 174.5 |
| 2 | 131.1 | 131.1 |
| 3 | 33.4 | 33.4 |
| 4 | 69.9 | 69.9 |
| 5 | 37.3 | 37.3 |
| 6 | 25.5 | 25.5 |
| 8 | 26.2 | 26.2 |
| 9 | 35.5 | 35.5 |
| 10 | 79.3 | 79.2 |
| 11 | 32.4 | 32.4 |
| 12 | 28.4 | 28.4 |
| 13 | 82.0 | 81.9 |
| 14 | 74.3 | 74.4 |
| 17 | 74.1 | 74.3 |
| 18 | 82.7 | 82.7 |

28

TABLE 15-continued $^{13}$C NMR (125 MHz, CDCl$_3$) Data 29 and 22

| C | 29$^a$ | 22$^b$ |
|---|---|---|
| 19 | — | — |
| 20 | — | — |
| 21 | 82.7 | 82.8 |
| 22 | 74.4 | 74.3 |
| 23 | 33.5 | 34.2 |
| 24 | 25.6 | 25.8 |
| 32 | 31.9 | 31.9 |
| 33 | 22.7 | 22.7 |
| 34 | 14.2 | 14.2 |
| 35 | 151.8 | 151.8 |
| 36 | 78.0 | 78.0 |
| 37 | 19.2 | 19.1 |

$^a$Signals of other methylene carbons appear approximately at δ 30.0, 29.7, 29.6, 29.4, 28.8, 28.7 and 28.4.
$^b$Signals of other methylene carbons appear approximately at δ 30.6, 29.8, 29.7, 29.6, 29.5, 29.4, 28.4, 28.2, and 28.1 using CHCl$_3$—MeOH (9:1) and hexaneacetone (3:2), respectively, and visualized with 5% phosphomolybdic acid in EtOH.

Bioassay. The extracts, fractions, and isolates were routinely evaluated for lethality to brine shrimp larvae (BST). Cytotoxicities against human solid tumor cells were measured at the Purdue Cell Culture Laboratory, Purdue Cancer Center, for the A-549 lung carcinoma, MCF-7 breast carcinoma, and HT-29 colon adenocarcinoma.

Plant Material. The stem bark of G. giganteus (B-826538, PR-50604) was collected in Thailand in September 1978 under the auspices of Dr. Robert E. Perdue, Medicinal Plant Laboratory, USDA, Beltsville, Md., where voucher specimens are maintained.

Extraction and Isolation. The residue of the 95% EtOH crude extract of 4 kg of the stem bark was partitioned between H$_2$O and CHCl$_3$ to give an H$_2$O layer and a CHCl$_3$ layer. The residue of the CHCl$_3$ layer was partitioned between hexane and 10% H$_2$O in MeOH to give a MeOH layer (ca. 100 g of dry residue) and a hexane layer. The MeOH residue, which represented the most active fraction in the BST test (LC$_{50}$ 15.1 µg/ml), was repeatedly chromatographed over Si gel columns directed by BST activity, using gradients of C$_6$H$_6$/E+OA/MeOH, hexane/EtOAc, and CHCl$_3$/MeOH and purified by HPLC, using hexane-MeOH-THF (90:9:1), to give a white wax of gonionenin (31 mg).

Oxidization and Cyclization of Gigantetronenin. Gigantetronenin (28) was available as previously isolated from G. Giganteus as described above. To gonionenin (90 mg, in 10 ml of CH$_2$Cl$_2$), was added m-chloroperbenzoic Acid (m-CPBA, 13 mg) and stirred for 1 hour at room temperature. The mixture was washed using 1% NaHCO$_3$ (5 ml) and H$_2$O (2×5 ml), and the CH$_2$Cl$_2$ layer was dried in vacuo to give the 21/22-epoxide of 28; to the 21/22 epoxide (in 10 ml of CH$_2$Cl$_2$) was added 30% perchloric acid (HCl O$_4$, 5 µl); the mixture was stirred for another hour at room temperature to give a mixture of gigantecin and C-18/21-cis-gigantecin. The mixture was washed using 1% NaHCO$_3$ (5 ml) and H$_2$O (2×5 ml), and the CH$_2$Cl$_2$ layer was dried in vacuo and resolved by HPLC to give 35 mg of 29 (yield: 38%) and 35 mg of 22 (yield: 37%).

Gigantecin (29). White wax, mp 109°–110 ° C., [α]D+ 5.3° (c 1.8, MeOH); UV λ$_{max}$: (MeOH) 212 nm (log E, 3.60), IR V$_{max}$ (film) 3453, 2918, 2850, 2360, 2340, 1754, 1728, 1469, 1322, 1059 cm–1, HRFABMS (glycerol) obsd 639.4841 (MH+), calcd for C$_{37}$H$_{67}$O$_8$ 639.4836. $^1$H and $^{13}$C NMR: see Tables 14 and 15, respectively.

C-18/21-cis-gigantecin (22). White wax, mp 89°–90 ° C., 6.7° (c 1.5, MeOH); UV λ$_{max}$: (MeOH) 212 nm (log E, 3.74), IR $V_{max}$: (film) 3440, 2918, 2851, 1754, 1726, 1468, 1306 cm$^{-1}$, HRFABMS (glycerol) obsd 639.4854 (MH+), calcd for $C_{37}H_{67}O_8$ 639.4836. $^1$H and $^{13}$C NMR: see Tables 14 and 15, respectively.

Acetylations. Compounds 29 and 22 (0.5 mg of each) were mixed with anhydrous pyridine/$Ac_2O$ at rt overnight and, through the usual workup, gave ca. 0.5 mg of the tetra-acetates 29a and 22a respectively. See Table 14.

TMS Derivatizations. Compounds 29 and 22 (ca. 0.3 mg of each) were treated with N,O-bis-(trimethylsilyl)-acetamide (20 μl) and pyridine (2 μl) and heated at 70° for 30 min to yield the respective tetra-TMS derivatives 20b and 22b.

An additional acetogenin, Goniocin, was isolated from the ethanolic extracts of the bark of *Goniothalamus giganteus* after partitionings and repeated chromatographic separations. Lethality of the fraction to the larvae of brine shrimp in the brine shrimp lethality test was used to guide the fractionation. The residue of the 95% EtOH crude extract of 4 kg of the stem bark was partitioned between $H_2O$ and $CHCl_3$. The residue of the $CHCl_3$ layer was partitioned between hexane and 10% $H_2O$ in MeOH to give 100 g of dry MeOH residue. The MeOH residue, which represented the most active fraction in the BST test ($LC_{50}$ 15.1 μg/ml), was repeatedly chromatographed over Si gel columns directed by BST activity, using gradients of $C_6H_6$/EtOAc/MeOH, hexane/EtOAc, and $CHCl_3$/MeOH and purified by HPLC over silica gel, using hexane-MeOH-THF (90:9:1), to give a white wax of goniocin.

Goniocin (23) represents a novel heterocyclic ring subclass in the series of Annonaceous acetogenins. This subclass is the adjacent tri-THF ring system. In the case of goniocin (23), the relative stereochemistry of this system is trans, threo, trans, threo, trans, and threo from C-10 to C-22. Goniocin (23) is a new prototype for a whole series of possible variations, whether they are natural or synthetic; and this new subclass is the tri-THF Annonaceous acetogenins.

On the basis of spectral data (Table 16), Goniocin was suggested to be a new acetogenin possessing a terminal α,β-unsaturated γ-lactone with a 4—OH group like gigantecin and gigantetronenin. The molecular formula of 23, $C_{37}H_{66}O_7$, having one more index of hydrogen deficiency than the bis-THF acetogenins, indicated that there were three THF rings in 23 since no extra double bond proton or carbon signals were observed in the NMR spectra. The adjacent tri-THF moiety in 23 was further identified by six proton signals at δ3.96–3.78 and six oxygenated carbon signals at δ83.0–79.6 (Table 16). The single carbinol carbon signal at δ74.3 (C-22), with its corresponding proton signal at δ3.37 (H-22) which had correlation cross peaks with the proton at δ3.80 (H-21) in the $^1$H—$^1$H COSY spectrum, showed that there was only one OH group in 23 adjacent to a THF ring. The carbon signal for C-10 at δ79.3 demonstrated the absence of an OH group adjacent to this side of the THF system.

TABLE 16

| | $^{13}$C NMR and $^1$H NMR Data of 23 and its S- and R-Mosher Esters. | | | |
|---|---|---|---|---|
| | $^{13}$C (125 MHz) | $^1$H (500 MHz) | | ΔδH |
| | 23 | 23 (J in Hz) | S-MPTA-23 | R-MPTA-23 | $δ_S-δ_P$ |
| 37 | 19.1 | 1.35 d (6.5) | 128 | 1.31 | neg |
| 36 | 78.0 | 5.06 qq (6.5, 1.5) | 4.86 | 4.91 | neg |
| 35 | 151.9 | 7.20 q (1) | 6.72 | 6.97 | neg |
| 1 | 174.3 | — | — | — | — |
| 2 | 131.1 | — | — | — | — |
| 3 | 33.2 | 2.53 dddd, 2.40 dddd | 2.57 | 2.64 | neg |
| 4 | 69.8 | 3.85 m | 5.31 | 537 | R |
| 5 | 37.2 | 1.47 m | 1.65 | 1.62 | pos |
| 6–8 | 29.7–25.4 | 1.60–1.2 m | 1.60–1.20 | 1.60–1.20 | — |
| 9 | 35.6 | 1.44 m | 1.43 | 1.42 | — |
| 10 | 79.6 | 3.93 m | 3.89 | 3.87 | — |
| 11 | 32.1 | 2.02 m, 1.62 m | 1.96, 1.62 | 1.96, 1.63 | — |
| 12, 15, 16 | 28.5–28.3 | 1.96 m, 1.70–1.64 m | 1.88–1.58 | 1.92–1.60 | — |
| 13, 14, 17, 18 | 82.3–81.1 | 3.92–3.83 m | 63.92–3.82 | 3.98–3.84 | — |
| 19 | 28.5 | 1.96 m, 1.64 m | 1.88–1.58 | 1.92–1.60 | — |
| 20 | 28.8 | 1.96 m, 1.60 m | 1.91, 1.49 | 2.02, 1.56 | neg |
| 21 | 83.0 | 3.80 m | 4.04 | 4.05 | neg |
| 22 | 74.2 | 3.37 m | 5.05 | 5.05 | R |
| 23 | 33.3 | 1.38 m | 1.62 | 1.50 | pos |
| 24 | 25.6 | 1.60–1.20 m | 1.29 | 1.18 | pos |
| 25–31 | 29.7–29.3 | 1.60–1.20 m | 1.60–1.20 | 1.60–1.20 | — |
| 32 | 31.9 | 1.60–1.20 | 1.60–1.20 | 1.60–1.20 | — |
| 33 | 22.7 | 1.28 m | 1.28 | 1.28 | — |
| 34 | 14.1 | 0.879 t (7.0) | 0.880 | 0.880 | — |

The placement of the tri-THF rings at C-10 through C-21 was determined by the EIMS fragmentation of the bis-TMSi derivative of 23.

The Ha and Hb proton signals of the THF methylenes (C-11, 12, 15, 16, 19, and 20) at δ2.02–1.96 and 1.70–1.62, respectively, those of H-13, 14, 17, and 18 at δ3.92–3.83, and that of H-22 at δ3.37 suggested that the relative stereochemistry around the tri-THF rings was trans-threo-trans-threo-trans-threo, from C-10 through C-22, by comparisons with the $^1$H NMR data of model compounds and other known acetogenins. Both of the absolute configurations of the carbinol stereocenters at C-4 and C-22 were determined to be R by preparation of Mosher ester derivatives (MTPA, Table 16). As the C-4 R and C-36 S relationship has always been found in the acetogenins, the absolute stereochemistry of 23 was proposed to be 4R, 10S, 13R, 14R, 17R, 17R, 18R, 21R, 22R, and 36S, as illustrated.

The level of bioactive potencies (Table 13) of goniocin (23) is comparable to that of adriamycin but is not at a par with bullatacin, bullatacinone, asimicin and their analogues. Our previous research has indicated that three hydroxyls (especially with one near the methyl terminus of the aliphatic chain) are necessary for enhanced potency within the adjacent bis-THF acetogenins subclass. Thus, the introduction of a third hydroxyl into the structure of the tri-THF compounds is anticipated to produce enhanced bioactive potencies. The introduction of such chemical changes to goniocin (23) would be difficult chemically, but the natural compounds very likely exist.

Various cancer cells, infectious organisms, and pests respond differently to acetogenins that are more or less hydrophobic. Formulations into various deliverable drug and pesticidal products require different levels of hydrophobicity. The increased hydrophobicity of the tri-THF acetogenins (vs. their bis-THF relatives) will enhance their applications and formulations in certain instances. Applications of these agents include uses as: single primary anticancer, anti-infective, antifungal, and other therapeutic agents, and as pesticidal agents; combination drugs/agents with other acetogenins and/or other compounds/drugs/agents; and as single or combination drug/and/agents against multiple (or single) drug-resistant cancers, other drug resistant diseases, and against resistant pests.

Annonaceous acetogenins are mainly composed of three groups, i.e., the adjacent bistetrahydrofuran (THF), non-adjacent bis-THF, and mono-THF subclasses. All of the acetogenins in these subclasses have multiple stereogenic centers, and, indeed, some are differentiated from each other only by their stereochemistries. Consequently, the determination of the relative and absolute stereochemistries of these stereocenters has become a major concern in the elucidation of the structures of new, as well as previously reported, acetogenin compounds. In addition, the stereochemistries, in many cases, influence the relative potencies and biological specificities.

Because of their waxy nature, the acetogenins and their derivatives do not readily produce crystals suitable for X-ray crystallographic analysis. Relative stereochemistries around the THF ring(s) and those of the ketolactone moieties have typically been determined by comparisons with synthetic model compounds of known relative stereochemistry. The absolute stereochemistry of none of the Annonaceous acetogenins had been defined until recently when Mosher ester methodology was applied and demonstrated to be very helpful. This methodology has been successfully used to determine the absolute configurations of the carbinol centers of several adjacent bis-THF and mono-THF acetogenins.

The non-adjacent bis-THF acetogenins are the newest subclass of the THF-bearing Annonaceous acetogenins, and some, e.g., bullatalicin, show promising in vivo antitumor activities although their potencies are less than those of the adjacent bis-THF compounds. Their non-adjacent bis-THF rings have made their structural elucidations and assignments of their relative stereochemistries more difficult than the adjacent bis-THF and mono-THF subclasses. Bullatalicin, published in 1989, was the second member of this subclass, and its relative stereochemistry and those of others in this subclass were clarified by applicants in 1993.

The refined Mosher ester methodology analyzes differences between the proton chemical shifts of S- and R-MTPA esters on both sides of the stereogenic carbinol centers. [Rieser, M. J.; Hui, Y.-H; Rupprecht, J. K.; Kozlowski, J. F.; Wood, K. V.; McLaughlin, J. L.; Hanson, P. R.; Zhuang, A.; Hoye, T. R.; *J. Am. Chem. Soc.* 1992, 114, 10203. However, this procedure cannot be applied to the non-adjacent THF acetogenins, such as bullatanocin (20), bullatalicin (18) and squamostatin A (13) because the hydroxyls between the two THF rings are only two carbons apart, and the phenyl rings of the Mosher esters interfere with each other. Additionally, it is not feasible to assign accurately, the complicated proton chemical shifts of the per-Mosher esters of these compounds. Therefore, until now, the absolute configurations of the non-adjacent bis-THF acetogenins has not been reported.

Similar problems are also encountered in the other subclasses of acetogenins that have hydroxyls in close proximity to each other, e.g., those having a vicinal diol like gigantetrocin A (10) and those having a 1,4-diol like goniothalamicin (8). In addition, the absolute configurations of non-THF-flanking carbinol centers, such as the C-28 of squamocin (16), have not been solved.

Structural Illustration 1

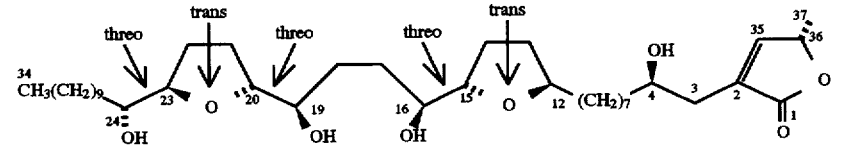

Bullatanocin (20)

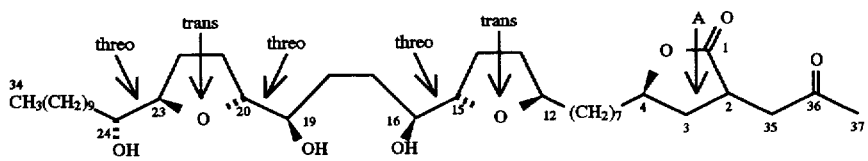

(2,4-cis)-Bullatanocinone (24a, A = cis)
(2,4-trans)-bullatanocinone (24b, A = trans)

Structural Illustration 1

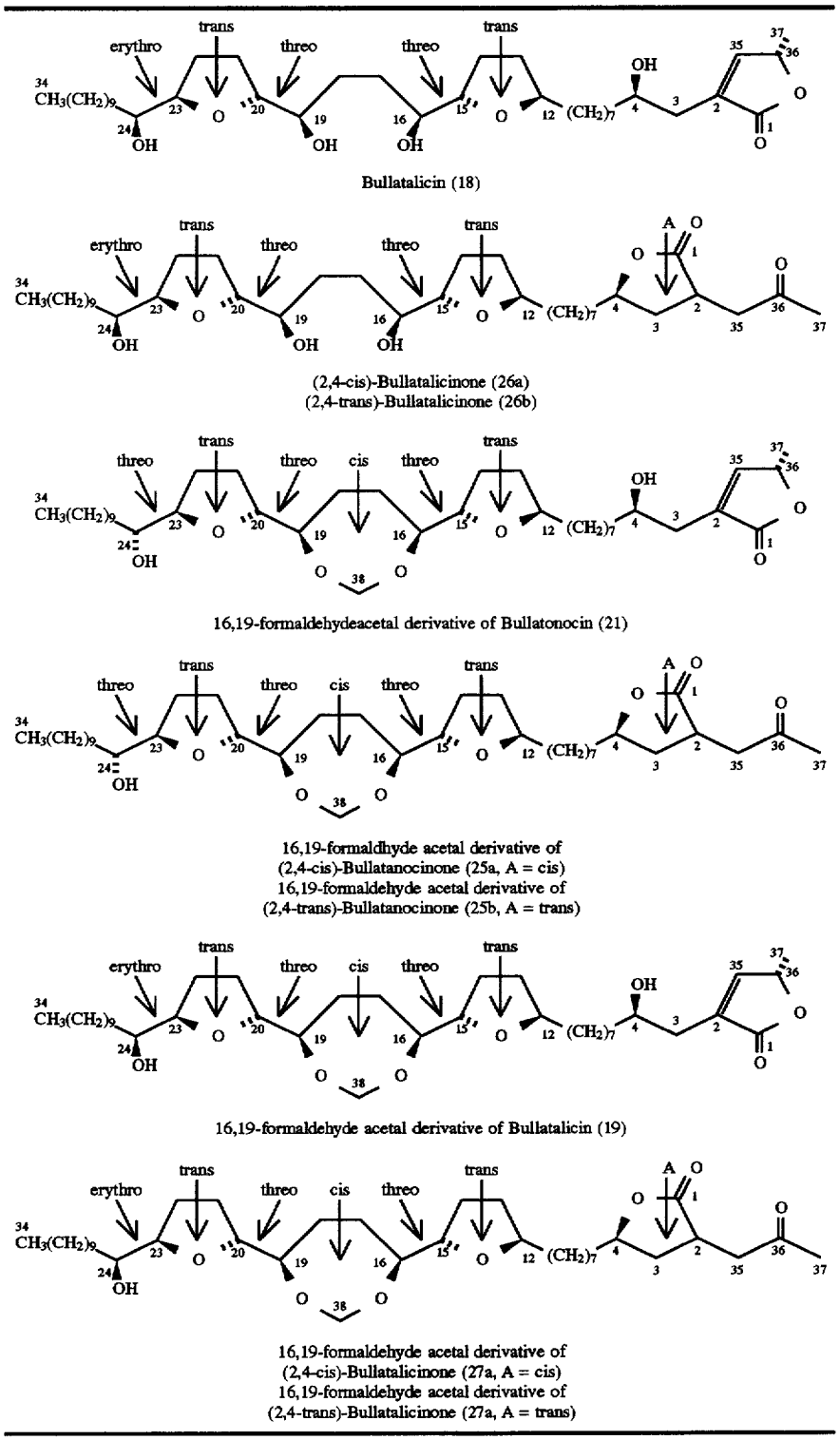

Bullatalicin (18)

(2,4-cis)-Bullatalicinone (26a)
(2,4-trans)-Bullatalicinone (26b)

16,19-formaldehydeacetal derivative of Bullatonocin (21)

16,19-formaldhyde acetal derivative of
(2,4-cis)-Bullatanocinone (25a, A = cis)
16,19-formaldehyde acetal derivative of
(2,4-trans)-Bullatanocinone (25b, A = trans)

16,19-formaldehyde acetal derivative of Bullatalicin (19)

16,19-formaldehyde acetal derivative of
(2,4-cis)-Bullatalicinone (27a, A = cis)
16,19-formaldehyde acetal derivative of
(2,4-trans)-Bullatalicinone (27a, A = trans)

Structural Illustration 2
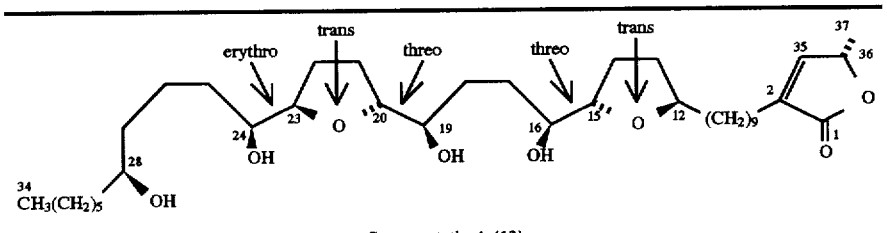
Squamostatin A (13)
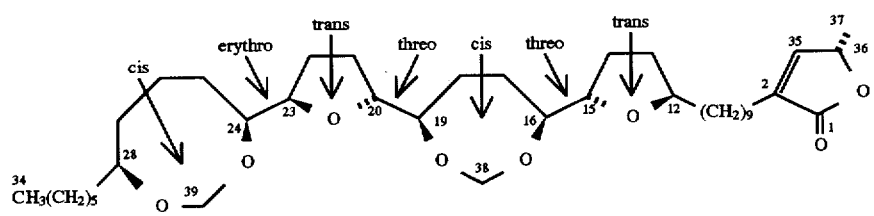
16,19- and 24,28-bis-formaldehyde acetal
derivative of Squamostatin A (14)
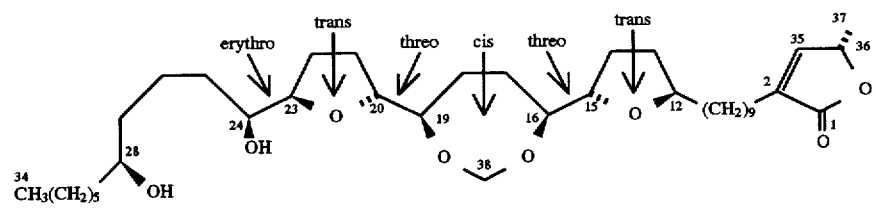
16,19-formaldehyde acetal derivative of Squamostatin A (15)
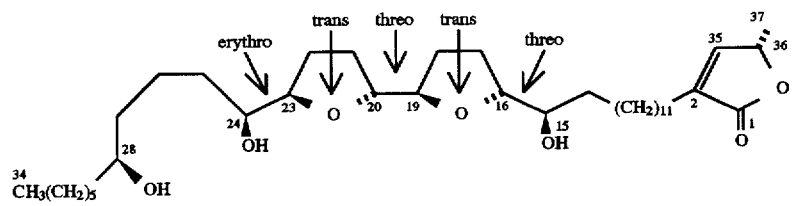
Squamocin (16)
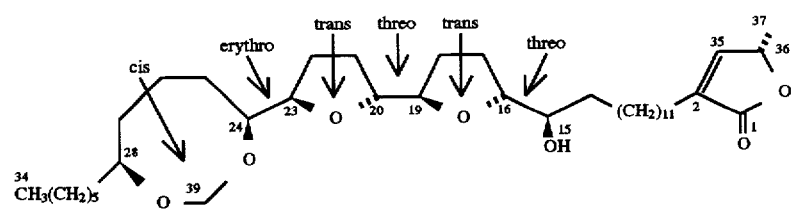
24,28-formaldehyde acetal deriviates of Squamocin (17)
Structural Illustration 3
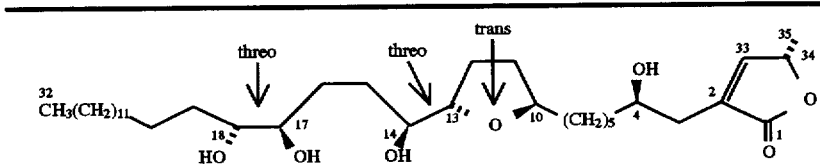

Structural Illustration 3

Gigantetrocin A (10)

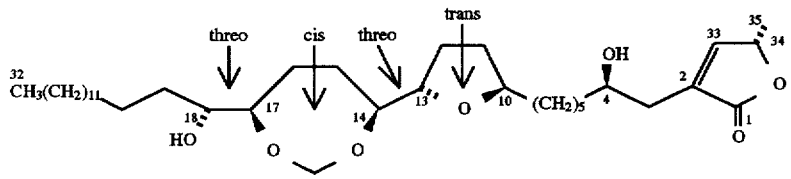

14,17-formaldehyde acetal derivative of gigantetrocin A (11)

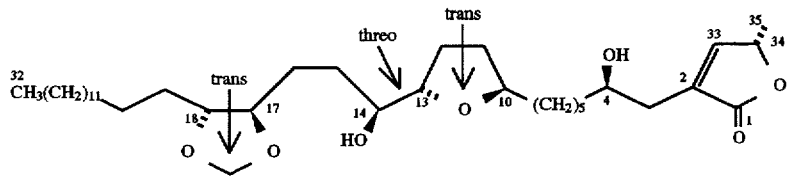

17,18-formaldehyde acetal derivative of Gigantetrocin A (12)

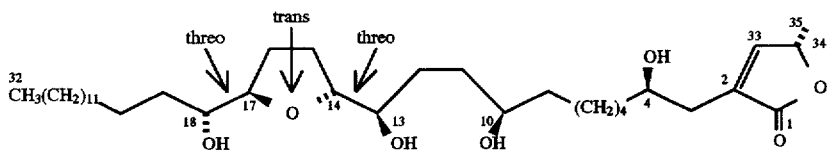

Goniothalamicin (8)

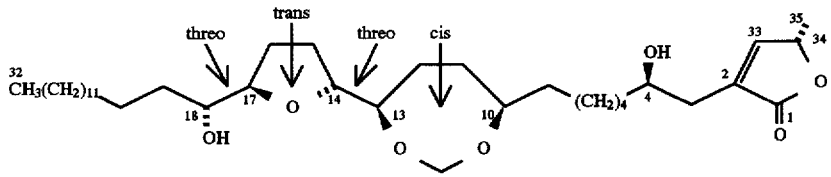

10,13-formaldehyde acetal derivative of Goniothalamicin (9)

---

Consequently, many Annonaceous acetogenins remain undefined stereochemically, and many continue to be introduced into the literature without determinations of their absolute stereochemistries.

Generally, the bis-THF acetogenins show much higher cytotoxic potencies than the mono-THF compounds, and their enhanced potency is also evident in their inhibition of intact mitochondria. In addition solving the absolute stereochemistries of the nonadjacent bis-THF acetogenins, we have also determined if the bioactivities of acetogenins is further enhanced as the number of rings is increased, i.e., by conversion of the mono-THF acetogenins to bis-ring compounds and the bis-THF compounds to tri- or tetra-ring compounds.

Mono-alcohols can be converted into intramolecular formaldehyde acetals using chlorotrimethylsilane (Me$_3$SiCl) and dimethyl sulfoxide (Me$_2$SO). Bal. B. S. and Pinnick, H. W., *Organic Chem.* 44, p. 3727 (1979). We have modified this method and successfully employed it to convert 1,2-, 1,4- and/or 1,5-diols of appropriate acetogenins into cyclic intramolecular formaldehyde acetals (Scheme II).

Scheme II

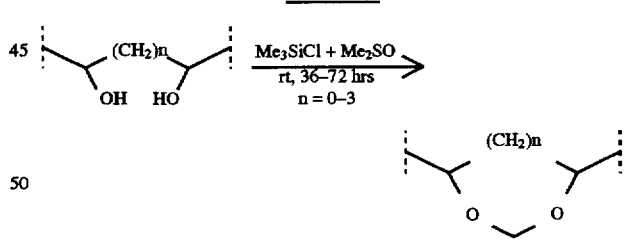

The acetal moiety which is formed connects the diols but does not change the stereochemistries of their carbinol centers. Significant differences in the $^1$H NMR spectra between the acetal protons in the cis or trans configurations of the cyclic formal derivatives then allows assignment of the relative stereochemistries of the diols in the parent compounds. Furthermore, the erythro configurations in 13, 18 and 26 can be definitely assigned at C-23/24 and not at C-15/16 or C-19/20 after this conversion, since in their respective acetal derivatives only the THF-flanking hydroxyl at C-24 is left free and the chemical shift of H-24 at δ3.82 clearly indicates that it is erythro.

Since this method does not affect other isolated hydroxyls, these groups, then, are free to be converted into Mosher esters. Consequently, the assignments of the proton chemical shifts affected by these Mosher esters become more feasible, i.e., the formulation decreases the number of hydroxyls, decreases the number of esters, and, hence, decreases the complication of proton signals affected by the Mosher esters in the esterified formal derivatives. With the relative stereochemistries around the THF ring(s) already in hand, from comparisons of $^1$H NMR spectra with those of model compounds, the absolute stereochemistries of all of the stereocenters can then be concluded by analyses of the $^1$H NMR data of S- and R-MTPA esters of the formal derivatives.

We have used the conversion to formaldehyde acetals and the subsequent application of the refined Mosher ester methodology, to determine the absolute stereochemistries of several *Annonaceous acetogenins*, each of which have 1,2- 1,4- and/or 1,5-diol moieties. Thus, for the first time, the absolute configurations of these compounds has been defined for the following compounds: bullatanocin (20), (2,4-cis and trans)-bullatanocinones (24a and 24b), bullatalicin (18) (2,4-cis and trans)-bullatalicinones (26a and 26b) squamostatin A (13), squamocin (16), gigantetrocin A (10), and goniothalamicin (8).

Many of the acetal derivatives show enhanced cytotoxicities, as compared to the parent compound, against human tumor cell lines (see data in Table 17 for comp. 21 vs. 20; 25 vs. 24; 15 vs. 13; and 19 vs. 18). Applicants have also determined that these acetal derivatives show similar bioactive potencies and selectivities, improving utilization of many of the natural acetogenins.

Preparation of Cyclic Intramolecular Acetogenins Formaldehyde Acetyl Derivatives To determine the absolute configurations of the Annonaceous acetogenins having vicinal 1,2-, 1,4-diol, and/or 1,5-diols, the diols are first converted into cyclic formaldehyde acetals.

It has been previously reported (Bal, D. S. and Pinnick, H. W., *Organic Chem.* 44, p. 3727(1979)) that monoalcohols can be converted to intramolecular acetogenins formaldehyde acetyl derivatives by mixing equivalent millimolar concentrations of mono-alcohols, Me$_3$SiCl, and Me$_2$SO and converted the mono-alcohols into intermolecular formaldehyde acetals. However, applicants found that adding equivalent millimolar concentrations of Me$_3$SiCl and Me$_2$SO to acetogenins having 1,2- 1,4-, and/or 1,5-diols, resulted in very low yields of cyclic intramolecular formaldehyde acetal derivatives, and the yields did not increase by lengthening the reaction times. Thin layer chromatography (TLC) showed an abundance of unreacted acetogenins.

By increasing the amount of Me$_3$SiCl and Me$_2$SO to 2-3-fold millimolar excesses over the starting acetogenins, the yields of the acetal derivatives increased to about 30% after 36–72 hrs reaction times. Because the reaction

TABLE 17

Bioactivities of Compounds 8–21, and 24–27.

| Compound | BST LC50 (µg/ml) | A-549 ED50 (µg/ml) | MCF-7 ED50 (µg/ml) | HT-29 ED50 (µg/ml) | RMB IC$_{50}$ (n moles/Lt/mg protein) |
|---|---|---|---|---|---|
| 20 | $4.30 \times 10^{-1}$ | $5.15 \times 10^{-10}$ | $2.42 \times 10^{-2}$ | $1.66 \times 10^{-11}$ | 50.7 |
| 21 | $6.50 \times 10^{-3}$ | $1.43 \times 10^{-11}$ | $2.22 \times 10^{-1}$ | $2.07 \times 10^{-13}$ | 11.3 |
| 24 | $2.80 \times 10^{-1}$ | $6.43 \times 10^{-4}$ | $2.93 \times 10^{-1}$ | $2.34 \times 10^{-8}$ | 61.1 |
| 25 | $1.50 \times 10^{-2}$ | $6.77 \times 10^{-5}$ | 1.28 | $7.01 \times 10^{-13}$ | 28.3 |
| 18 | 1.20 | $1.22 \times 10^{-10}$ | $2.82 \times 10^{-5}$ | $6.48 \times 10^{-8}$ | 19.2 |
| 19 | $4.90 \times 10^{-2}$ | $1.28 \times 10^{-13}$ | $1.85 \times 10^{-2}$ | $9.10 \times 10^{-13}$ | 27.8 |
| 26 | $4.70 \times 10^{-1}$ | $5.62 \times 10^{-5}$ | $1.57 \times 10^{-3}$ | $2.42 \times 10^{-13}$ | 23.0 |
| 27 | $3.80 \times 10^{-2}$ | $3.69 \times 10^{-9}$ | $6.39 \times 10^{-2}$ | $2.25 \times 10^{-13}$ | 20.5 |
| 13 | 2.80 | $2.68 \times 10^{-4}$ | $7.20 \times 10^{-6}$ | $2.04 \times 10^{-11}$ | — |
| 14 | 10.2 | 1.78 | $1.00 \times 10^{-3}$ | $2.89 \times 10^{-7}$ | — |
| 15 | $7.00 \times 10^{-3}$ | $4.87 \times 10^{-9}$ | 1.09 | $3.03 \times 10^{-13}$ | — |
| 16 | $2.00 \times 10^{-2}$ | $2.49 \times 10^{-12}$ | $3.03 \times 10^{-2}$ | $1.91 \times 10^{-13}$ | 21.5 |
| 17 | $4.40 \times 10^{-3}$ | $2.37 \times 10^{-10}$ | $6.95 \times 10^{-1}$ | $2.89 \times 10^{-13}$ | 421.1 |
| 16 | $6.00 \times 10^{-1}$ | $4.52 \times 10^{-8}$ | $3.55 \times 10^{-4}$ | $3.06 \times 10^{-12}$ | 287.1 |
| 11 | — | $7.98 \times 10^{-4}$ | $4.61 \times 10^{-1}$ | $7.30 \times 10^{-13}$ | — |
| 12 | $7.50 \times 10^{-3}$ | $6.95 \times 10^{-2}$ | $2.58 \times 10^{-1}$ | $3.57 \times 10^{-12}$ | 290.3 |
| 8 | 37.0 | $7.11 \times 10^{-6}$ | $5.73 \times 10^{-4}$ | $1.71 \times 10^{-9}$ | 554.8 |
| 9 | $5.38 \times 10^{-2}$ | 1.05 | $4.09 \times 10^{-4}$ | $2.19 \times 10^{-5}$ | 203.1 |
| Adriamycin | $8.00 \times 10^{-2}$ | $4.19 \times 10^{-3}$ | $4.01 \times 10^{-1}$ | $3.55 \times 10^{-2}$ | — |
| Rotenone | $1.23 \times 10^{-2}$ | — | — | — | — |

All of the samples were tested in the same run in each bioassay except in the MBT, in which the parent compounds and their respective acetal derivatives were tested in the same run; Adriamycin and Rotenone are included as a positive antitumor control standards.

BST = Brine shrimp lethality test
A-549 = Human lung carcinoma
MCF-7 = Human breast carcinoma
HT-29 = Human colon adenocarcinoma
RMB = Rat mitochondrial bioassey enhancements in a bioassay that quantifies the inhibition of oxygen uptake by rat liver mitochondria (see Table 17, RMB data), demonstrating the site of their biological action is identical to that of their parent acetogenins. Thus, the addition of the acetal rings has not created a new, unanticipated mode of cytotoxic action, but rather enhances the produces HCl, which causes decomposition of the acetogenins, further elongation of the reaction time did not increase, but, conversely, decreased the product yields. Some unreacted acetogenins can be recovered when purifying the acetal products.

Formulation of the formaldehyde acetal derivatives

Bullatanocin (20, Illustration 1 has two nonadjacent THF rings and three THF flanking hydroxyls; all of the hydroxyls possess the threo relative stereochemical relationships with their respective rings. The $^1$H NMR spectra of the S- and R-per-MTPA esters of 20 were too complicated to permit confident assignments. 20 was treated with excesses of Me$_3$SiCl and Me$_2$SO at room temperature for 48 hrs to give a stable product which was identified as the 16,19-formaldehyde acetal derivative (21, yield: 30%). The structure of 21 (Illust. 1) was determined by the $^1$H and $^{13}$C NMR data and confirmed by the HRFABMS [obsd 651.4828, calcd 651.4836, for C$_{38}$H$_{66}$O$_8$ (MH+)] and the EIMS fragmentation of its bis-TMSi derivative. The downfield shifts of two hydroxy methine (H-16 and 19) protons from δ3.41 in 20 to δ3.66 and 3.63 in 21 and the appearance of two doublets (J=7.5 Hz) at δ5.26 and 4.63 (the acetal protons), in the $^1$H NMR spectrum of 21 (Table 18), and a carbon signal at δ95.8 (the acetal carbon), in the $^{13}$C NMR spectrum of 21, confirmed the formation of an acetal ring in 21. These NMR data also indicated that the newly formed acetal ring possessed the cis relative configuration, and, thus, revealed either an S/R or an R/S relative configuration between C-16 and C-19. Two hydroxylated methine protons at δ3.84 and 3.39 in the $^1$H NMR spectra of 21 shifted downfield to δ5.31 and 5.06 in S-MTPA-21 and to δ5.37 and 5.05 in R-MTPA-21 and further demonstrated that only two hydroxyls, at C-4 and C-24, remained free in 21. The assignments of the proton chemical shifts of the Mosher esters of 21 were relatively easy, because the phenyl rings were separated by nineteen carbons, too far apart to interfere with each other. The $^1$H NMR data for the bis-S- and R-MTPA-21 are summarized in Table 18. C-24 was assigned to have the R absolute configuration, since the sign of Δ&H ($\Delta\delta_H(\delta_s-\delta_R)$) is positive for the chain side, showing relatively more shielding for this side in R-MTPA-21, and negative for the THF ring side, showing relatively more shielding for this side in S-MTPA-21. As the relative stereochemistry from C-12 to C-24 of 20 was already known, the absolute configurations of C-12 (R), C-15 (S), C-16 (S), C-19 (R), C-20 (R), and C-23 (R) were readily concluded. The configuration at C-4 was determined to be R, according to the data listed in Table 18, and C-36 was assigned as S, based on the usual ubiquitous 4R, 36S relationship. Thus, the absolute configuration of bullatanocin (20) is proposed as illustrated in Illustration 1.

(2,4-Cis and trans)bullatanocinones (24a and 24b, Illustration 1) are a pair of ketolactone acetogenins differing from each other only in the configuration of the 2,4-bisubstituted-γ-lactone ring. Because of the close similarity of their structures, such 2,4-cis and trans ketolactone acetogenins are very difficult to separate, and they are usually isolated and reported as a pair of isomers. The structures of 24a and 24b are very similar to that of 20 except that they possess the ketolactone moiety instead of the α,β-unsaturated γ-lactone ring. Thus, the skeletons and relative stereochemistries around the non-adjacent bis-THF rings of 24a and 24b are the same as those of 20. Compounds 24a and 24b as a mixture, were converted into the formaldehyde acetal derivatives [25a and 25b, yield: 30%, HRFABMS: obsd 651.4836, calcd 651.4836, for C$_{38}$H$_{67}$O$_8$(MH$^+$)]. The cis-configuration of the acetal ring was indicated by the two doublets (J=7.5 Hz) for the acetal

TABLE 18

$^1$H NMR Data of 21, 19 S- and R-Per-MTPA-21, and S- and R-Per-MTPA-10 [δ ppm (J = Hz)].

| Proton | 21 | S-21 | R-21 | $\Delta\delta_H(\delta_s-\delta_P)$ | 19 | S-19 | R-21 | $\Delta\delta_H(\delta_s-\delta_P)$ |
|---|---|---|---|---|---|---|---|---|
| 37 | 1.44 d (7.0) | 1.29 d (7.0) | 1.32 d (7.0) | neg | 1.43 d (7.0) | 1.29 d (7.0) | 1.32 d (7.0) | neg |
| 36 | 5.06 qq | 4.86 qq | 4.91 qq | neg | 5.07 qq | 4.86 qq | 4.91 qq | neg |
| 35 | 7.19 q (1.5) | 6.72 q (1.5) | 6.98 q (1.5) | neg | 7.19 q (1.5) | 6.72 q (1.5) | 6.98 q (1.5) | neg |
| 3a | 2.53 ddtd | 2.60 | 2.68 | neg | 2.53 ddtd | 2.60 | 2.68 | neg |
| 3b | 2.40 ddt | 2.58 | 2.60 | neg | 2.40 ddt | 2.58 | 2.60 | neg |
| 4 | 3.84 m | 5.31 m | 5.37 m | R* | 3.84 m | 5.31 m | 5.37 m | R* |
| 5 | 1.47 m | 1.64 m | 1.62 m | pos | 1.47 m | 1.65 m | 1.62 m | pos |
| 6–10 | 1.40–1.20 | 1.40–1.20 | 1.40–1.20 | — | 1.40–1.20 | 1.40–1.20 | 1.40–1.20 | — |
| 11a | 1.47 m | 1.47 m | 1.47 m | — | 1.48 m | 1.48 m | 1.48 m | — |
| 11b | 1.40 m | 1.38 m | 1.38 m | — | 1.42 m | 1.40 m | 1.38 m | — |
| 12 | 3.95 m | 3.94 m | 3.94 m | — | 3.96 m | 3.94 m | 3.94 m | — |
| 13a | 2.01 m | 2.01 m | 2.01 m | — | 2.00 m | 2.02 m | 2.02 m | — |
| 13b | 1.64 m | 1.62 m | 1.61 m | — | 1.64 m | 1.64 m | 1.63 m | — |
| 14a | 1.96 m | 1.93 m | 1.93 m | — | 2.00 m | 1.94 m | 1.94 m | — |
| 14b | 1.66 m | 1.62 m | 1.61 m | — | 1.63 m | 1.64 m | 1.64 m | — |
| 15 | 3.99 m | 3.98 m | 3.99 m | — | 4.06 m | 4.01 m | 4.00 m | — |
| 16 | 3.66 m | 3.59 m | 3.63 m | neg | 3.62 m | 3.62 m | 3.62 m | — |
| 17a, 18a | 1.87 m | 1.82 m | 1.92 m | neg | 1.87 m | 1.88 m | 1.84 m | pos |
| 17b, 18b | 1.79 m | 1.70 m | 1.76 m | neg | 1.79 m | 1.76 m | 1.72 m | pos |
| 38a | 5.26 d (7.5) | 5.21 d (7.5) | 5.22 d (7.5) | neg | 5.29 d (7.5) | 5.28 d (7.5) | 5.23 d (7.5) | pos |
| 38b | 4.63 d (7.5) | 4.56 d (7.5) | 4.56 d (7.5) | –0 | 4.64 d (7.5) | 4.62 d (7.5) | 4.57 d (7.5) | pos |
| 19 | 3.63 m | 3.61 m | 3.63 m | neg | 3.62 m | 3.62 m | 3.54 m | pos |
| 20 | 4.01 m | 3.94 m | 4.02 m | neg | 4.00 m | 3.95 m | 3.74 m | pos |
| 21a | 1.96 m | 1.75 m | 1.93 m | neg | 2.00 m | 1.90 m | 1.82 m | pos |
| 21b | 1.66 m | 1.63 m | 1.77 m | neg | 1.63 m | 1.67 m | 1.60 m | pos |
| 22a | 1.97 m | 1.91 m | 2.03 m | neg | 1.90 m | 1.93 m | 1.85 m | pos |
| 22b | 1.64 m | 1.51 m | 1.59 m | neg | 1.83 m | 1.79 m | 1.70 m | pos |
| 23 | 3.84 m | 4.08 m | 4.08 m | –0 | 3.94 m | 4.13 m | 4.05 m | pos |
| 24 | 3.39 m | 5.06 m | 5.05 m | R* | 3.88 m | 5.33 m | 5.29 m | S* |
| 25 | 1.40 m | 1.62 m | 1.47 m | pos | 1.35 m | 1.60 m | 1.62 m | neg |
| 26 | 1.40–1.20 | 1.30 m | 1.14 m | pos | 1.40–1.20 | 1.20 m | 1.30 m | pos |
| 27–33 | 1.40–1.20 | 1.40–1.20 | 1.40–1.15 | — | 1.40–1.20 | 1.40–1.20 | 1.40–1.20 | — |
| 34 | 0.878 t (7.0) | 0.882 t (7.0) | 0.883 t (7.0) | — | 0.878 t (7.0) | 0.883 t (7.0) | 0.882 t (7.0) | — |
| MeO-1 | — | 3.52 s | 3.50 s | — | — | 3.52 s | 3.50 s | — |

TABLE 18-continued

| | ¹H NMR Data of 21, 19 S- and R-Per-MTPA-21, and S- and R-Per-MTPA-10 [δ ppm (J = Hz)]. | | | | | | | |
|---|---|---|---|---|---|---|---|---|
| Proton | 21 | S-21 | R-21 | Δδ$_H$(δ$_S$–δ$_P$) | 19 | S-19 | R-21 | Δδ$_H$(δ$_S$–δ$_P$) |
| MeO-24 | — | 3.55 s | 3.64 s | — | — | 3.54 s | 3.56 s | — |
| Ar-10H | — | 7.63–7.37 | 7.65–7.36 | — | — | 7.63–7.37 | 7.65–7.36 | — |

*Absolute configuration of carbinol center.

protons, present at δ5.27 and 4.63, in the ¹H NMR spectra (Table 19) of 25a and 25b. C-24 was determined to have the R configuration from comparisons of the ¹H NMR data of S- and R-MTPA esters of 25a and 25b. These data suggested that 24a and 24b, as expected, have the same absolute configurations in the non-adjacent bis-THF moiety as those in 20. The (2,4-cis and trans)-ketolactone acetogenins can be chemically prepared from the original 4-hydroxylated α,β-unsaturated γ-lactone acetogenins. In the conversion, the configuration at C-4 will not be changed. Because the R configuration has been found to be universal in all of the natural 4-hydroxylated acetogenins whose absolute stereochemistries have been revealed, the absolute configurations of C-4 in 24a and 24b were, thus, also assigned as 4R. Thus, the absolute configuration of 2,4-cis-bullatanocinone (24a) is proposed to be 2R, 4R, 12R, 15S, 16S, 19R, 20R, 23R, and 24R, and that of 2,4-trans-bullatanocinone (24b) is proposed to be 2S, 4R, 12R, 15S, 16S, 19R, 20R, 23R, and 24R.

Since there was only one free hydroxyl left in 25a and 25b, in the ¹H NMR spectra of 5-and R-MTPA esters of 25a and 25b, the shielding distance that a single Mosher ester could affect was easily observed. The data listed in Table 19 show that the shielding effect of the phenyl ring could reach at least eight bonds from the chiral carbon center (C-24). This observation can be very useful in determining the absolute stereochemistries of isolated chain carbinol centers, because, in those situations, it is often impossible to differentiate and make chemical shift assignments of the methylene protons closest to the carbinol center. However, the small, but very stable and reproducible, chemical shift differences of the protons on the oxygenated carbons or the terminal methyl group, located several bonds from the carbinol center, can be

TABLE 19

| | ¹H NMR Data of 25a and 25b, 27a and 27b, S- and R-MTPA-25a and 25b, and S- and R-MTPA-27a and 27b (δ ppm (J = Hz)] | | | | | | | |
|---|---|---|---|---|---|---|---|---|
| Proton | 24a & 25b | S-25a & -25b | R-25a & -25b | Δδ$_H$(δ$_S$–δ$_R$) | 27a & 27b | S-27a & -27b | R-27a & -27b | Δδ$_H$(δ$_S$–δ$_R$) |
| 2 cis | 3.02 m | 3.02 m | 3.02 m | — | 3.02 m | 3.02 m | 3.02 m | — |
| trans | 3.03 m | 3.03 m | 3.03 m | — | 3.03 m | 3.03 m | 3.03 m | — |
| 3a cis | 1.48 m | 1.48 m | 1.48 m | — | 1.48 m | 1.48 m | 1.48 m | — |
| trans | 2.23 dddd | 2.23 dddd | 2.23 dddd | — | 2.23 dddd | 2.23 dddd | 2.23 dddd | — |
| 3b cis | 2.61 dddd | 2.61 dddd | 2.61 dddd | — | 2.61 dddd | 2.61 dddd | 2.61 dddd | — |
| trans | 1.99 m | 1.99 m | 1.99 m | — | 1.99 m | 1.99 m | 1.99 m | — |
| 4 cis | 4.39 dddd | 4.39 dddd | 1.39 dddd | — | 4.39 dddd | 4.39 dddd | 4.39 dddd | — |
| trans | 4.54 dddd | 4.54 dddd | 4.54 dddd | — | 4.54 dddd | 4.54 dddd | 4.54 dddd | — |
| 5a cis | 1.76 m | 1.76 m | 1.76 m | — | 1.76 m | 1.76 m | 1.76 m | — |
| trans | 1.71 m | 1.71 m | 1.71 m | — | 1.71 m | 1.71 m | 1.71 m | — |
| 5b cis | 1.60 m | 1.60 m | 1.60 m | — | 1.60 m | 1.60 m | 1.60 m | — |
| trans | 1.58 m | 1.58 m | 1.58 m | — | 1.58 m | 1.58 m | 1.58 m | — |
| 6–10 | 1.40–1.20 | 1.40–1.20 | 1.40–1.20 | — | 1.40–1.20 | 1.40–1.20 | 1.40–1.20 | — |
| 11a | 1.47 m | 1.47 m | 1.47 m | — | 1.48 m | 1.48 m | 1.48 m | — |
| 11b | 1.40 m | 1.38 m | 1.38 m | — | 1.42 m | 1.40 m | 1.38 m | — |
| 12 | 3.95 m | 3.94 m | 3.94 m | — | 3.94 m | 3.95 m | 3.95 m | — |
| 13a | 2.01 m | 2.00 m | 2.00 m | — | 2.00 m | 2.02 m | 2.02 m | — |
| 13b | 1.64 m | 1.62 m | 1.61 m | — | 1.64 m | 1.64 m | 1.63 m | — |
| 14a | 1.96 m | 1.93 m | 1.93 m | — | 2.00 m | 1.95 m | 1.94 m | — |
| 14b | 1.66 m | 1.62 m | 1.62 m | — | 1.63 m | 1.65 m | 1.64 m | — |
| 15 | 4.00 m | 3.98 m | 4.01 m | neg | 4.04 m | 4.03 m | 4.00 m | pos |
| 16 | 3.67 m | 3.59 m | 3.63 m | neg | 3.62 m | 3.63 m | 3.61 m | pos |
| 17a, 18a | 1.87 m | 1.82 m | 1.92 m | neg | 1.87 m | 1.86 m | 1.86 m | pos |
| 17b, 18b | 1.79 m | 1.73 m | 1.78 m | neg | 1.79 m | 1.78 m | 1.71 m | pos |
| 38a | 5.27 d (7.5) | 5.21 d (7.5) | 5.22 d (7.5) | neg | 5.29 d (7.5) | 5.26 d (7.5) | 5.23 d (7.5) | pos |
| 38b | 4.63 d (7.5) | 4.56 d (7.5) | 4.56 d (7.5) | –0 | 4.64 d (7.5) | 4.59 d (7.5) | 4.57 d (7.5) | pos |
| 19 | 3.63 m | 3.58 m | 3.63 m | neg | 3.62 m | 3.61 m | 3.54 m | pos |
| 20 | 4.01 m | 3.93 m | 4.01 m | neg | 4.01 m | 3.95 m | 3.74 m | pos |
| 21a | 1.96 m | 1.76 m | 1.93 m | neg | 2.00 m | 1.88 m | 1.80 m | pos |
| 21b | 1.66 m | 1.62 m | 1.77 m | neg | 1.63 m | 1.66 m | 1.61 m | pos |
| 22a | 1.97 m | 1.92 m | 2.04 m | neg | 1.90 m | 1.92 m | 1.83 m | pos |
| 22b | 1.64 m | 1.52 m | 1.57 m | neg | 1.83 m | 1.78 m | 1.70 m | pos |
| 23 | 3.84 m | 4.08 m | 4.08 m | –0 | 3.94 m | 4.13 m | 4.05 m | pos |
| 24 | 3.39 m | 5.06 m | 5.05 m | R* | 3.88 m | 5.33 m | 5.28 m | S* |
| 25 | 1.40 m | 1.63 m | 1.47 m | pos | 1.35 m | 1.57 m | 1.62 m | neg |
| 26 | 1.30–1.20 | 1.30 m | 1.14 m | pos | 1.30–1.20 | 1.20 m | 1.30 m | neg |
| 27–33 | 1.40–1.20 | 1.40–1.20 | 1.40–1.20 | — | 1.40–1.20 | 1.40–1.20 | 1.40–1.20 | — |
| 34 | 0.878 t (7.0) | 0.881 t (7.0) | 0.883 t (7.0) | — | 0.878 t (7.0) | 0.883 t (7.0) | 0.881 t (7.0) | — |

TABLE 19-continued

¹H NMR Data of 25a and 25b, 27a and 27b, S- and R-MTPA-25a and 25b, and S- and R-MTPA-27a and 27b (δ ppm (J = Hz)]

| Proton | 24a & 25b | S-25a & -25b | R-25a & -25b | $\Delta\delta_H(\delta_S-\delta_R)$ | 27a & 27b | S-27a & -27b | R-27a & -27b | $\Delta\delta_H(\delta_S-\delta_R)$ |
|---|---|---|---|---|---|---|---|---|
| 35a cis | 2.61 dd | 2.61 dd | 2.61 dd | — | 2.61 dd | 2.61 dd | 2.61 dd | — |
| trans | 2.67 dd | 2.67 dd | 2.67 dd | — | 2.67 dd | 2.67 dd | 2.67 dd | — |
| 35b cis | 3.11 dd | 3.11 dd | 3.11 dd | — | 3.11 dd | 3.11 dd | 3.11 dd | — |
| trans | 3.04 dd | 3.04 dd | 3.04 dd | — | 3.04 dd | 3.04 dd | 3.04 dd | — |
| 37 | 2.20 s | 2.20 s | 2.20 s | — | 2.20 s | 2.20 s | 2.20 s | — |
| MeO-24 | — | 3.56 s | 3.64 s | — | — | 3.54 s | 3.56 s | — |
| Ar-5H | — | 7.63–7.37 | 7.65–7.36 | — | — | 7.63–7.37 | 7.65–7.36 | — |

*Absolute configuration of carbinol center.

clearly observed in the ¹H NMR spectra of the respective S- and R-MTPA derivatives.

Bullatalicin (18, Illustration 1) has the same skeleton of contiguous atoms as 20. However, 18 possesses two hydroxyls having threo and one hydroxyl having erythro relative stereochemical relationships with the THF rings. In 20, all three of the hydroxyls are threo to their respective THF rings. When 18 was first published, the erythro relationship was erroneously assigned at C-15/16. This assignment was subsequently found to be incorrect by careful study of the COSY spectrum of 18, and the location of the erythro linkage was revised to be at C-23/24 by the use of double relayed COSY spectra and by comparisons with the structures of other acetogenins from the same source. Since the proton chemical shifts of H-16 and H-19 of 18 were very close to each other and the off-diagonal crosspeaks between H-16 and H-19 in the double relayed COSY spectrum of 18 were weak, we wished to verify this. After 18 was converted into the 16,19-formaldehyde acetal derivative (19, Illustration 1), using Me₃SiCl and Me₂SO, both proton signals at δ3.41 in 18, which are assigned to the protons on the hydroxylated carbons having threo relationships with the THF rings, shifted downfield to δ3.62 in 19, and the proton signal at δ3.88 in 18, which is assigned to the proton on the hydroxylated carbon having an erythro relationship with its THF ring, remained almost unchanged in 19 (Table 18) vs. 18. Thus, the fact that a free hydroxyl having an erythro relationship with its THF ring remained at C-24 in 19, confirmed the placement of the erythro linkage at C-23/24 in 18. Again, the acetal protons in 19, appearing as two doublets at δ5.29 and 4.64, respectively, suggested an R/S or an S/R relative stereochemical relationship between C-16 and C-19. Bis S- and R-MTPA esters of 19 were then prepared, and their ¹H NMR data are reported in Table 18. The absolute configurations of C-4 and C-24 were determined to be R and S, respectively, by the striking change of the signs of the $\Delta\delta_H(\delta_S-\delta_R)$ values on the two sides of the chiral centers (Table 18). The data thus demonstrates that 18 differs from 20 only in the absolute stereochemistry at C-24 (S in 18 and R in 20). The structure of 18, showing the proposed absolute configurations (4R, 12R, 15S, 16S, 19R, 20R, 23R, 24S, 36S), is illustrated in Illustration 1.

(2,4-Cis and trans)-bullatalicinones (26a and 26b, Illustration 1) are another pair of ketolactone acetogenins, isolated and reported as a mixture of the two isomers. As with the relationship between bullatanocin (20) and its ketolactones (24a and 24b), 26a and 26b possess the same skeletons and relative stereochemistries around the nonadjacent bis-THF rings as those of bullatalicin (18). In the ¹H NMR spectrum of their 16,19-formaldehyde acetal derivatives (27a and 27b, Table 19), the acetal proton signals presented two doublets at δ5.29 and 4.64 (J=7.5) and suggested the cis configuration of the newly formed acetal ring. The chemical shift of H-24, the only proton left on an hydroxylated carbon in 27a and 27b, appeared at δ3.88, the same as in 19, and this observation placed the erythro linkage at C-23/24 in 26a and 26b. Consequently, the S- and R-MTPA esters of 27a and 27b were prepared, and the ¹H NMR and COSY spectra of these esters were recorded. These data (Table 19) further demonstrated that the influence of a mono-MTPA, as in the S- and R-MTPA esters of 25a and 25b, could extend over at least 8 bonds. The $\Delta\delta_H(\delta_S-\delta_R)$ values (Table 19) determined the S absolute configuration at C-24. Thus, as illustrated in Illustration 1, the absolute configuration of 2,4-cis-bullatalicinone (26a) was concluded to be 2R, 4R, 12R, 15S, 16S, 19R, 20R, 23R, and 24S and that of 2,4-trans-bullatalicinone (26b) was concluded to be 2S, 4R, 12R, 15S, 16S, 19R, 20R, 23R, and 24S.

Squamostatin A (13, Illustration 2) was originally published without determination of any stereochemistry. Its relative stereochemistry was assigned recently by applicants, but its absolute stereochemistry remained unknown. The C-28 hydroxyl made the direct determination of its absolute configuration more complicated because the acetal reaction can convert both 1,4 and 1,5 diols into acetal rings and complete conversion would leave no free hydroxyl available in 13 for making Mosher esters to determine the absolute stereochemistry. However, we predicted that the formation of a seven membered acetal ring from a 1.4 diol should be faster than the formation of an eight membered acetal ring from a 1,5-diol. The conversion of 13 to the formaldehyde acetal derivatives was carefully performed, and the progress was checked by TLC every 4 hours. The reaction was terminated after 36 hours when almost all of the starting material had disappeared and two major products had appeared; the two products were purified by HPLC. The ¹H NMR data of the two products (Table 20) indicated, just as predicted, that one product was the 16,19-mono-formaldehyde acetal derivative (15, Illustration 2) of 13 and the other, which was much less polar than 15 on TLC, was the 16,19- and 24,28-bis-formaldehyde acetal derivative (14, Illustration 2) of 13. The two pairs of doublets at δ5.27/4.62 and 5.10/4.56 in the ¹H NMR spectrum (Table 20) of 14 suggested that both formaldehyde acetal rings possessed the cis relative configuration, and indicated either an R/R or an S/S relative relationship between C-24 and C-28 and either an R/S or an S/R relative relationship between C-16 and C-19 in 13; the latter indication was confirmed by the $^1$H NMR spectrum of 15, in which the acetal protons also appeared as two doublets at δ5.29 and 4.64 and were almost the same signals as those of 19. Table 20 lists the $^1$H NMR data of the S- and R-MTPA esters of 15 and the $\Delta\delta_H(\delta_S-\delta_R)$ values.

TABLE 20

$^1$H NMR Data of 14 and 15, and S- and R-PER-MTPA-15 [δ ppm (J = Hz)]

| Proton | 14 | 15 | S-15 | R-15 | $\Delta\delta_H(\delta_S-\delta_R)$ |
|---|---|---|---|---|---|
| 37 | 1.41 d (7.0) | 1.41 d (7.0) | 1.41 d (7.0) | 1.41 d (7.0) | — |
| 36 | 5.00 qq | 5.00 qq | 5.00 qq | 5.00 qq | — |
| 35 | 6.99 q | 6.99 q | 6.93 q | 6.93 q | — |
| 3 | 2.26 tt | 2.26 tt | 2.26 tt | 2.26 tt | — |
| 4–10 | 1.40–1.20 | 1.40–1.20 | 1.40–1.20 | 1.40–1.20 | — |
| 11 | 1.50 m | 1.50 m | 1.50 m | 1.50 m | — |
| 12 | 3.94 m | 3.94 m | 3.95 m | 3.95 m | — |
| 13a | 2.02 m | 2.02 m | 2.03 m | 2.02 m | — |
| 13b | 1.48 m | 1.47 m | 1.49 m | 1.48 m | — |
| 14a | 1.98 m | 2.01 m | 1.95 m | 1.95 m | — |
| 14b | 1.64 m | 1.64 m | 1.64 m | 1.62 m | — |
| 15 | 4.03 m | 4.04 m | 4.01 m | 4.00 m | — |
| 16 | 3.62 m | 3.62 m | 3.63 m | 3.60 m | pos |
| 17a, 18a | 1.82 m | 1.82 m | 1.86 m | 1.82 m | — |
| 17b, 18b | 1.68 m | 1.76 m | 1.77 m | 1.72 m | pos |
| 38a | 5.27 d (7.5) | 5.29 d (7.5) | 5.28 d (7.5) | 5.23 d (7.5) | pos |
| 38b | 4.62 d (7.5) | 4.64 d (7.5) | 4.61 d (7.5) | 4.56 d (7.5) | pos |
| 19 | 3.62 m | 3.62 m | 3.61 m | 3.53 m | pos |
| 20 | 4.00 m | 4.01 m | 3.93 m | 3.73 m | pos |
| 21a | 1.98 m | 2.01 m | 1.89 m | 1.82 m | pos |
| 21b | 1.64 m | 1.65 m | 1.66 m | 1.60 m | pos |
| 22a | 1.98 m | 1.90 m | 1.90 m | 1.81 m | pos |
| 22b | 1.92 m | 1.83 m | 1.77 m | 1.66 m | pos |
| 23 | 3.92 m | 3.92 m | 4.08 m | 3.95 m | pos |
| 24 | 3.70 m | 3.89 m | 5.57 m | 5.19 m | S* |
| 25 | 1.63, 1.43 | 1.48, 1.40 | 1.57 m | 1.57 m | –0 |
| 26 | 1.40–1.20 | 1.40–1.20 | 1.40–1.20 | 1.40–1.20 | — |
| 27 | 1.40 m | 1.47 m | 1.57 m | 1.51 m | pos |
| 28 | 3.54 m | 3.60 m | 5.02 m | 5.03 m | S* |
| 29 | 1.22 m | 1.42 m | 1.57 m | 1.60 m | neg |
| 30–33 | 1.40–1.20 | 1.40–1.20 | 1.40–1.20 | 1.40–1.20 | — |
| 34 | 0.877 t (7.0) | 0.883 t (7.0) | 0.862 t (7.0) | 0.877 t (7.0) | neg |
| 39a | 5.10 d (7.5) | — | — | — | — |
| 39b | 4.56 d (7.5) | — | — | — | — |
| MeO-24 | — | — | 3.54 s | 3.54 s | — |
| MeO-28 | — | — | 3.53 s | 3.52 s | — |
| Ar-10H | — | — | 7.60–7.37 | 7.60–7.37 | — |

*Absolute configuration of carbinol center.

Although the $\Delta\delta_H(\delta_S-\delta_R)$ of H-25 gave a zero value as it was adversely affected by the Mosher ester at C-28, the $\Delta\delta_H(\delta_S-\delta_R)$ values of the protons on the THF ring side of the chiral center at C-24, as far away as to H-16, showed universally positive values. This permitted us to conclude that the absolute configuration at C-24 is S and that at C-28 is also S. As noted above, in conducting the analyses of the $^1$H NMR data of the S- and R-MTPA esters of 25a and 25b and the S- and R-MTPA esters of 27a and 27b, we had observed that the shielding influence of an MTPA moiety could reach at least eight bonds. It was, furthermore, very interesting to find that the $\Delta\delta_H(\delta_S-\delta_R)$ value of the terminal methyls (C-34) of the S- and R-MTPA esters of 15 was –7.5 Hz (Table 20) and was affected sufficiently for the application of Mosher's methodology; this result similarity suggested an S absolute configuration for C-28.

Squamocin (16, Illustration 2) is an adjacent bis-THF acetogenin which has, so far, been reported from four Annonaceous plants. Its relative stereochemistry was determined by an X-ray crystallographic study of a derivative, but its absolute stereochemistry was not solved, since the absolute configuration at C-28 could not be determined. To solve this problem, the hydroxyls at C-24 and C-28 were converted into the formaldehyde acetal (17) whose $^1$H NMR data (Table 21) showed the same relative stereochemical relationship (R/R or S/S) between C-24 and C-28 as that previously revealed by X-ray diffraction. This result also demonstrated that the relative stereochemistry of such diols could be accurately predicted by their acetal derivatives. After the absolute configuration at C-15 was determined to be S by analyses of the $^1$H NMR data of the S- and R-MTPA esters of 17, these absolute stereochemistries of the other chiral centers, around the bis-THF rings and at C-28, were determined by tracing their relative stereochemistries. Squamocin (16)

TABLE 21

$^1$H NMR Data of 17, and S- and R-PER-MTPA-16, and S- and R-PER-MTPA-17, [δ ppm (J = Hz)]

| Proton | S-16 | R-16 | Δδ$_H$(δ$_S$–δ$_R$) | 17 | S-17 | R-17 | Δδ$_H$(δ$_S$–δ$_R$) |
|---|---|---|---|---|---|---|---|
| 37 | 1.41 d (7.0) | 1.41 d (7.0) | — | 1.41 d (7.0) | 1.41 d (7.0) | 1.41 d (7.0) | — |
| 36 | 5.00 qq | 5.00 qq | — | 5.00 qq | 5.00 qq | 5.00 qq | — |
| 35 | 6.93 q | 6.93 q | — | 6.93 q | 6.93 q | 6.93 q | — |
| 3 | 2.26 tt | 2.26 tt | — | 2.26 tt | 2.26 tt | 2.26 tt | — |
| 4–12 | 1.40–1.20 | 1.40–1.20 | — | 1.40–1.20 | 1.40–1.20 | 1.40–1.20 | — |
| 13 | 1.30 m | 1.13 m | pos | 1.40–1.20 | 1.33 m | 1.14 m | pos |
| 14 | 1.61 m | 1.46 m | pos | 1.39 m | 1.63 m | 1.50 m | pos |
| 15 | 5.06 m | 5.03 m | R* | 3.59 m | 5.06 m | 5.05 m | R* |
| 16 | 4.03 m | 3.99 m | pos | 3.82 m | 4.05 m | 4.045 m | –0 |
| 17a | 1.92 m | 2.01 m | neg | 1.95 m | 1.89 m | 2.02 m | neg |
| 17b | 1.52 m | 1.55 m | neg | 1.62 m | 1.50 m | 1.57 m | neg |
| 18a | 1.80 m | 1.87 m | neg | 1.95 m | 1.72 m | 1.92 m | neg |
| 18b | 1.65 m | 1.74 m | neg | 1.62 m | 1.61 m | 1.70 m | neg |
| 19 | 3.79 m | 3.82 m | neg | 3.85 m | 3.79 m | 3.89 m | neg |
| 20 | 3.79 m | 3.63 m | pos | 3.90 m | 3.84 m | 3.89 m | neg |
| 21a | 1.80 m | 1.68 m | pos | 1.95 m | 1.87 m | 1.92 m | neg |
| 21b | 1.65 m | 1.56 m | pos | 1.60 m | 1.59 m | 1.70 m | neg |
| 22a | 1.82 m | 1.75 m | pos | 1.95 m | 1.87 m | 1.94 m | neg |
| 22b | 1.68 m | 1.57 m | pos | 1.80 m | 1.71 m | 1.73 m | neg |
| 23 | 3.96 m | 3.87 m | pos | 3.91 m | 3.80 m | 3.82 m | neg |
| 24 | 5.21 m | 5.14 m | S* | 3.68 m | 3.61 m | 3.61 m | — |
| 25 | 1.55 m | 1.55 m | –0 | 1.64, 1.44 | 1.40 m | 1.42 m | — |
| 26 | 1.40–1.20 | 1.40–1.20 | — | 1.40–1.20 | 1.40–1.20 | 1.40–1.20 | — |
| 27 | 1.58 m | 1.50 m | pos | 1.62 m | 1.62 m | 1.60 m | — |
| 28 | 4.99 m | 5.03 m | S* | 3.55 m | 3.54 m | 3.55 m | — |
| 29 | 1.47 m | 1.53 m | neg | 1.62 m | 1.57 m | 1.57 m | — |
| 30–33 | 1.40–1.20 | 1.40–1.20 | — | 1.40–1.20 | 1.40–1.20 | 1.40–1.20 | — |
| 34 | 0.860 t (7.0) | 0.875 t (7.0) | neg | 0.878 t (7.0) | 0.877 t (7.0) | 0.878 t (7.0) | — |
| 38a | — | — | — | 5.10 d (7.5) | 5.08 d (7.5) | 5.09 d (7.5) | — |
| 38b | — | — | — | 4.56 d (7.5) | 5.53 d (7.5) | 5.53 d (7.5) | — |
| MeO-15 | — | — | — | — | 3.56 s | 3.64 s | — |
| MeO-28 | — | — | — | — | — | — | — |
| Ar-H | — | — | — | — | 7.65–7.35 | 7.65–7.35 | — |

*Absolute configuration of carbinol center.

has the same skeleton and relative configurations around the adjacent bis-THF rings as those of bullatacin and bullatacinone, and the above results showed that 16 also possesses the same absolute configuration within this moiety. At C-28, 16 was concluded to be S, and by checking the Δδ$_H$(δ$_S$–δ$_R$) value of the terminal methyl (C-34) of the S- and R-per-MTPA esters of 16, a negative value similarity suggested the S absolute configuration at C-28. This latter observation, as mentioned above in the discussion of squamostatin A (13), will be helpful to the stereochemical elucidations of several new acetogenins having a chain hydroxyl close to the terminal methyl (at positions C28 to C-32). In such cases, it is not feasible to assign the chemical shifts of the methylene protons that are close to the chain carbinol centers in the $^1$H NMR spectra of the Mosher esters of these compounds, but the absolute configuration of such chain carbinol centers can be easily solved by simply observing the Δδ$_H$(δ$_S$–δ$_R$) values of the terminal methyls.

Gigantetrocin A (10, Illustration 3) is a mono-THF acetogenin having a 1,4,5-triol moiety, and the analyses of the $^1$H NMR spectra of the S- and R-per-MTPA esters of 10 failed to solve the absolute configuration of 10. In addition, the triol group was anticipated to produce a mixture of formaldehyde acetal derivatives which would complicate the determination of the absolute configurations of the carbinol centers. Nevertheless, 10 was treated with excesses of Me$_3$SiCl and Me$_2$SO for 36 hrs. Following the routine procedures, two products were purified by HPLC. Just as predicted, the major product (yield: 35 %) was the 17,18-formaldehyde acetal derivative (12) of 10, and the minor product (yield: 4%) was the 14,17- formaldehyde acetal derivative (11) of 10, demonstrating that it is much easier to form a five membered acetal ring than to form a seven membered acetal ring. The increase of molecular weights to 608 in both products (HRFABMS: obsd 609.4730 in 11 and 609.4714 in 12 for MH$^+$, calcd. 609.4730) and the appearance of the acetal proton signals (at δ5.28 and 4.62 in 11 and at & 4.96 in 12) in their respective $^1$H NMR spectra confirmed the formation of the acetal moiety in both 11 and 12. The structures of 11 and 12 were further confirmed by their $^1$H and $^{13}$C NMR, COSY, and the EIMS data of their TMS derivatives. The fragment peak at m/z 299 in the EIMS of 11, in particular, proved the formation of its acetal at C-14 and C-17, and that at m/z 309 in the EIMS of 12 placed its acetal at C-17 and C-18. The acetal protons appeared as a doublet at δ5.28 and 4.62 in the $^1$H NMR spectrum of 11 and indicated the cis configuration for the newly formed acetal ring, and the acetal protons presented a singlet at δ4.96 in the $^1$H NMR spectrum of 12 and indicated the trans configuration for the newly formed, acetal ring. The latter data suggested that the vicinal diol at C-17, 18 in 10 possesses a threo configuration. The same result was previously obtained by analysis of the $^1$H NMR of the acetonide derivative of 10. The S- and R-MTPA esters of 12 were then prepared, and C-14 was determined to have the S absolute configuration. Since the relative stereochemical relationship between C-14 and C-17 was already revealed to be either S/R or R/S, the absolute configuration at C-17 was concluded to be R. The absolute configuration at C-4 was also R, as indicated by the Δδ$_H$(δ$_S$–δ$_R$) values in Table 22. The structure of 10, showing the proposed absolute configuration (4R, 10R, 13S, 14S, 17R, 18R, and 36S), is illustrated in Illustration 4.

Careful readers may have noticed that the $\Delta\delta_H(\delta_S-\delta_R)$ value of H-13 of the S- and R-MTPA esters of 12 (Table 22) been previously solved. A particular problem in determination of the absolute configuration of goniothalamicin is

TABLE 22

¹H NMR Data of 11, 12, and S- and R-PER-MTPA-12 [δ ppm (J = Hz)]

| Proton | 11 | 12 | S-12 | R-12 | $\Delta\delta_H(\delta_S-\delta_R)$ |
|---|---|---|---|---|---|
| 35 | 1.44 d (7.0) | 1.43 d (7.0) | 1.29 d (7.0) | 1.32 d (7.0) | neg |
| 34 | 5.06 qq | 5.07 qq | 4.86 qq | 4.91 qq | neg |
| 33 | 7.19 q | 7.19 q | 6.72 q | 6.98 q | neg |
| 3a | 2.53 ddt | 2.54 ddt | 2.60 | 2.68 | neg |
| b | 2.40 ddt | 2.40 ddt | 2.58 | 2.60 | neg |
| 4 | 3.84 m | 3.86 m | 5.31 m | 5.37 m | R* |
| 5 | 1.48 m | 1.48 m | 1.69 m | 1.65 m | pos |
| 6–8 | 1.40–1.20 | 1.40–1.20 | 1.40–1.20 | 1.40–1.20 | — |
| 9 | 1.53 m | 1.53 m | 1.47 m | 1.43 m | pos |
| 10 | 3.96 m | 3.88 m | 3.88 m | 3.78 m | pos |
| 11a | 2.02 m | 2.02 m | 2.01 m | 1.88 m | pos |
| 11b | 1.48 m | 1.52 m | 1.47 m | 1.40 m | pos |
| 12a | 1.96 m | 1.98 m | 2.02 m | 1.96 m | pos |
| 12b | 1.64 m | 1.61 m | 1.60 m | 1.56 m | pos |
| 13 | 4.00 q | 3.78 q | 4.00 q | 4.02 q | –0.02 |
| 14 | 3.61 m | 3.40 m | 5.08 m | 5.09 m | S* |
| 15a | 1.88 m | 1.86 m | 1.79 m | 1.90 m | neg |
| 15b | 1.80 m | 1.40 m | 1.50 m | 1.68 m | neg |
| 16 | 1.85 m | 1.57 m | 1.50 m | 1.55 m | neg |
| 17 | 3.52 m | 3.52 m | 3.30 m | 3.46 m | neg |
| 18 | 3.47 m | 3.52 m | 3.32 m | 3.47 m | neg |
| 36a | 5.28 d (7.5) | 4.96 s | 4.92 s | 4.96 s | neg |
| 36b | 4.62 d (7.5) |  | 4.89 s | 4.93 s | neg |
| 19 | 1.41 m | 1.57 m | 1.43 m | 1.47 m | neg |
| 20–31 | 1.40–1.20 | 1.40–1.20 | 1.40–1.20 | 1.40–1.20 | — |
| 32 | 0.880 t (7.0) | 0.880 t (7.0) | 0.880 t (7.0) | 0.880 t (7.0) | — |
| MeO-4 | — | — | 3.51 s | 3.50 s | — |
| MeO-14 | — | — | 3.66 s | 3.53 s | — |
| Ar-10H | — | — | 7.60–7.37 | 7.60–7.37 | — |

*Absolute configuration of carbinol center.

is –0.02 ppm and not a positive value as it is supposed to be. Nevertheless, the conclusion of the R absolute configuration at C-14 seems to be unambiguous since all of the other $\Delta\delta_H(\delta_{S-\delta R})$ values of the protons on both sides of C-14 consistently showed either positive (on the THF ring side) or negative (on the chain and acetal ring side) values. The converse value of H-13 might be caused from different conformations of the THF and acetal rings in the S- and R-MTPA esters of 12. The $\Delta\delta_H(\delta_{S-\delta R})$ values of such THF flanking protons (H-23 in the S- and R-MTPA esters of 21, 25a and 25b, H-16 in the S- and R-MTPA esters of 17, and H-17 in the S- and R-MTPA esters of 9) were found to be about zero if the carbinol centers have a threo relative stereochemical relationship with the THF ring.

The relative stereochemistries of the vicinal diols in Annonaceous acetogenins are usually determined by observing the chemical shifts of the acetenyl methyl protons in the ¹H NMR spectra of their acetonide derivatives, i.e., one singlet at δ1.37 indicates threo, and two separate singlets at δ1.43 and 1.33 indicate erythro. The acetonide derivative decomposes very easily, and the decomposition can occur during the purification procedure or even in the NMR tube in CDCl₃ during spectral analyses. In some cases, the proton signals of the acetenyl methyls are not distinct since they are usually overlapped with the large envelope of methylene proton signals. However, the formaldehyde acetal derivatives are relatively stable, and the acetal proton signals, located downfield from the aliphatic methylene proton signals, can be easily observed. Thus, formaldehyde acetal derivatization can also be used as a convenient method for determination of the relative stereochemistry of vicinal diols.

Goniothalamicin (8, Illustration 3) is a common mono-THF acetogenin, whose absolute stereochemistry has not focused on C-10. The formaldehyde acetal derivative (9) was prepared, and the analyses of the $\Delta\delta_H$ ($\delta_{S-\delta R}$) values of the S- and R-MTPA esters of 9 resulted in the determination of the absolute configuration at C-18 to be 18R; those at C-13, C-14, and C-17 were then all solved to be R by tracing their relative stereochemistries. The absolute configuration at C-10 was subsequently concluded to be also 10R, since an R/R or an S/S relative configuration relationship, between C-10 and C-13, had been revealed by the observation of the acetal protons which presented as a pair of doublets at δ5.16 and 4.61 (J=7.5 Hz) in the ¹H NMR spectrum of 9 (Table 23). The Mosher esters also demonstrated that the absolute configuration at C-4 was R, as usual with all acetogenins that have a 4-OH. The structure of 8, showing the proposed absolute configuration (4R, 10R, 13R, 14R, 17R, 18R, and 36S), is illustrated in Illustration 3.

Experimental Detail for Preparation and Characterization of Cyclic Acetols

General Information. Bullatanocin (20), (2,4-cis and trans)-bullatanocinones (24a and 24b), bullatalicin (18) (2,4-cis and trans)-bullatalicinones (26a and 26b) squamocin (16), gigantetrocin A (10), and goniothalamicin (8), were available as isolated in our laboratory from several plant species in the Annonaceae. Squamostatin A (13) was isolated from Annona squamosa and provided by Bayer AG, Germany.

¹H NMR, 2D COSY, and ¹³C NMR spectra, all in CDCl₃, were recorded on a Varian vXR-500S spectrometer. Proton chemical shifts were referenced to TMS (δ0.00) and carbon chemical shifts were referenced to CDCl₃ (δ77.0). All proton chemical shifts >δ2.10 were determined directly

TABLE 23

$^1$H NMR Data of 9 and S- and R-PER-MTPA-9 [δ ppm (J = Hz)]

| Proton | 9 | S-9 | R-9 | $\Delta\delta_H(\delta_S - \delta_R)$ |
|---|---|---|---|---|
| 35 | 1.43 d (7.0) | 1.28 d (7.0) | 1.31 d (7.0) | neg |
| 34 | 5.06 qq | 4.86 qq | 4.91 qq | neg |
| 33 | 7.19 q | 6.72 q | 6.97 q | neg |
| 3a | 2.53 ddt | 2.60 | 2.68 | neg |
| b | 2.40 ddt | 2.58 | 2.60 | neg |
| 4 | 3.84 m | 5.31 m | 5.37 m | R* |
| 5 | 1.47 m | 1.65 m | 1.61 m | pos |
| 6 | 1.40 ~ 1.20 | 1.30 m | 1.24 m | pos |
| 7 ~ 8 | 1.40 ~ 1.20 | 1.40 ~ 1.20 | 1.40 ~ 1.20 | — |
| 9 | 1.58 m | 1.72, 1.55 m | 1.73 m | — |
| 10 | 3.66 m | 3.60 m | 3.62 m | — |
| 11 | 1.80 m | 1.80, 1.66 m | 1.87 m | — |
| 12 | 1.80 m | 1.72, 1.54 m | 1.73 m | — |
| 13 | 3.66 m | 3.62 m | 3.63 m | — |
| 14 | 3.99 q | 3.92 q | 4.02 q | neg |
| 15a | 1.98 m | 1.75 m | 1.92 m | neg |
| b | 1.70 m | 1.65 m | 1.79 m | neg |
| 16a | 1.98 m | 1.91 m | 2.03 m | neg |
| b | 1.64 m | 1.52 m | 1.60 m | neg |
| 17 | 3.84 q | 4.08 q | 4.08 q | ~0 |
| 18 | 3.39 q | 5.05 q | 5.05 q | R* |
| 19 | 1.40 m | 1.60 m | 1.48 m | pos |
| 20 | 1.40 ~ 1.20 | 1.30 m | 1.14 m | pos |
| 21 ~ 31 | 1.40 ~ 1.20 | 1.40 ~ 1.20 | 1.40 ~ 1.20 | — |
| 32 | 0.880 t (7.0) | 0.880 t (7.0) | 0.882 t (7.0) | — |
| 36a | 5.16 d (7.5) | 5.11 d (7.5) | 5.11 d (7.5) | — |
| b | 4.61 d (7.5) | 4.54 d (7.5) | 4.53 d (7.5) | — |
| MeO-4 | — | 3.52 s | 3.50 s | — |
| MeO-18 | — | 3.56 s | 3.54 s | — |
| Ar-10H | — | 7.60 ~ 7.37 | 7.60 ~ 7.37 | — |

*Absolute configuration of carbinol center.

from the $^1$D $^1$H NMR spectra, whereas, because of the large degree of overlap among the resonances, all shifts <δ2.10 were carefully estimated from the centers of the relevant 2D COSY off-diagonal peaks. Mass spectral data were obtained on Finnigan 4000 or Kratos MS50 spectrometers. All of the reagents are Aldrich products.

Preparation and Purification of Formaldehyde Derivatives

To Me$_3$SiCl (100 mg, in 3 ml of CH$_2$Cl$_2$) was added Me$_2$SO (100 mg in 2 ml CH$_2$Cl$_2$), and the mixture was allowed to stand at room temperature for about one hr until a white precipitate appeared. The CH$_2$Cl$_2$ was decanted, and the white precipitate was quickly washed with 1 ml of CH$_2$Cl$_2$. To this precipitate, the starting acetogenin (30–60 mg, in 5 ml of CH$_2$Cl$_2$) was added with stirring at room temperature for 36–72 hrs, until almost all of the starting material had disappeared as determined by TLC. The mixture was washed using 1% NaHCO$_3$ (5 ml) and H$_2$O (2×5 ml), and the CH$_2$Cl$_2$ layer was dried in vacuo. The products were purified by normal phase open column chromatography (0.5% MeOH in CHCl$_3$) or HPLC [5–10% MeOH:THF (9:1) in hexane]. Yields were 25–40% and unreacted starting materials were often recovered.

Preparation and Purification of Mosher Esters

To an acetogenin or a formaldehyde derivative of an acetogenin (0.5–1 mg, in 0.3 ml of CH$_2$Cl$_2$) were sequentially added pyridine (0.2 ml), 4-(dimethylamino)pyridine (0.5 mg), and 25 mg of (R)-(−)-α-methoxy-α-(trifloromethyl)-phenylacetyl chloride. The mixture was stirred at room temperature for 4 hrs and passed through a disposable pipet (0.6×6 cm) containing silica gel (60–200 mesh) and eluted with 3 ml of CH$_2$Cl$_2$. The CH$_2$Cl$_2$ residue, dried in vacuo, was redissolved in CH$_2$Cl$_2$ and washed using 1% NaHCO$_3$ (5 ml) and H$_2$O (2×5 ml); the CH$_2$Cl$_2$ layer was dried in vacuo to give the S-Mosher esters. Using S-(+)-α-methoxy-α-(trifloromethyl)phenylacetyl chloride gave the R-Mosher esters. Both yields were typically higher than 90%.

TMS Derivatizations

Compounds (ca. 0.3 mg of each) were treated with N, O-bis(trimethylsilyl)acetamide (20 µl) and pyridine (2 µl) and heated at 70° for 30 minutes to yield the respective tetra-TMS derivatives.

Bioassays

The brine shrimp lethality test (BST), on newly hatched naupleii, was performed in our laboratory as previously described. McLaughlin, *Methods in Plant Biochemistry*, Vol. 6, Hostettmann, Academic Press, London, pp. 1–33 (1991). Seven day cytotoxicities against human solid tumor cells were measured at the Cell Culture Laboratory, Purdue Cancer Center, for the A-549 lung carcinoma, MCF-7 breast carcinoma, and HT-29 colon adenocarcinoma. The respiratory functions of rat liver mitochondria (RMB) were measured polarographically by determination of their rates of oxygen consumption after the addition of acetogenins or their derivatives.

Derivatizations of Acetogenins 16,19-Formaldehyde acetal derivative of bullatanocin (21): 60 mg of bullatanocin (20) was converted into 18 mg of 21 (yield: 30%) as a white wax; HRFABMS: obsd 651.4828, calcd 651.4836, for C38H6708 (MN+). $^1$H NMR: see Table 18; $^{13}$C NMR δ95.8 (C-38, acetal carbon), 81.0 (C-19), 80.3 (C-16).

4,24-TMSi derivative of 21: EIMS m/z (rel. int. %) 624 (12.5), 594 (28.6), 563 (11.4), 551 (43.1), 533 (II.I), 521 (27.0), 503 (36.3), 485 (16.3), 483 (14.8), 473 (18.1), 461 (18.9), 455 (28.8), 420 (22.1), 413 (39.0), 407 (22.6), 395 (24.6), 391(17.1), 381 (53.2), 352(22.9), 339(33.1), 335 (25.2), 323 (33.2), 313 (45.7), 309(30.6), 299 (37.3), 293 (37.9), 291(33.5), 275 (33.8), 273 (30.7), 269 (44.2), 257 (25.8), 249 (24.1), 243 (70.8), 239 (29.6), 229 (33.7), 227 (35.2), 223 (47.7), 213 (69.4), 199(32.4), 191(36.6), 184 (69.1), 169 (100.0).

4,24-S- and R-MTPA esters of 11: White oil-like; $^1$H NMR: see Table 22.

16,19-Formaldehyde acetal derivatives of (2,4-cis and trans)-bullatanocinones (25a and 25b): 50 mg of (2,4-cis and trans)-bullatanocinones (24a and 24b) was converted into 15 mg of 25a and 25b (yield: 30.0%) as a white oil; HPFABMS: obsd 651.4836, calcd 651.4836, for C38H6708 (MH+); $^1$H NMR: see Table 22.

24-TMSi derivates of 25a and 25b: EIMS m/z (rel. int. %) 745(100.0, M+Na), 479 (6.6), 449(3.3), 413(6.5), 313(9.8), 309(27.9), 291(3.2)243(100.0), 141(27.0).

24-S- and R-MTPA esters of 25a and 25b: White oil-like; $^1$H NMR: see Table 19.

16,19-Formaldehyde acetal derivative of bullatalicin (19): 80 mg of bullatalicin (18) was converted into 22 mg of 19 (yield: 27.5%) as a white wax; HRFABMS: obsd 651.4817, calcd 651.4836, for C$_{38}$H$_{67}$O$_8$ (MH+); $^1$H NMR: see Table 22; $^{13}$C NMR δ95.7 (C-38, acetal carbon), 81.7 (C-19), 80.3 (c-16).

4,24-TMSi derivative of 19: EIMS m/z (rel. int. %) 624 (26.6), 594 (38.3), 563 (13.8), 551(100.0), 533(16.0), 521 (35.2), 503(67.2), 485(7.0), 455(7.7), 420(8.0), 413 (21.9), 407(9.7), 395(12.0), 391(7.4), 381 (64.7), 352(11.2), 339 (12.6), 313(30.2), 309 (9.5), 293 (12.7), 291(15.0), 275 (30.7), 273 (12.0), 269(26.5), 243 (100.0), 229(13.1), 227 (11.1), 223(16.6), 213(57.2).

4,24-S- and R-MTPA esters of 19: White oil-like; $^1$H NMR: see Table 18.

16,19-Formaldehyde acetal derivatives of (2,4-cis and trans)-bullatalicinones (27a and 27b): 40 mg of (2,4-cis and trans)-bullatalicinones (26a and 26b) was converted into 13 mg of 25a and 25b (yield: 32.5%) as a white oil;

HRFABMS: obsd 651.4823, calcd 651.4836, for C38H6708 (MH+); $^1$H NMR: see Table 19.

24-TMSi derivatives of 27a and 27b: EIMS m/z (rel. int. %) 722 (16.4 %, M+), 479 (4.1), 449(3.6), 413(4.4), 383 (14.0), 367 (33.5), 339 (20.7), 313 (13.7), 309 (32.4), 291 (6.4) 269 (16.6), 243 (75.7), 213 (11.7), 141 (18.4).

24-S- and R-MTPA esters of 27a and 27b: White oil-like; $^1$H NMR: see Table 19.

Formaldehyde acetal derivatives of squamostatin A: 9 mg of squamostatin A (13) was converted into 1 mg of 16,19- and 24,28-bis-formaldehyde acetal derivative (14) of 13 [yield: 11.1%, white oil-like, HRFABMS: obsd 663.4852, calcd 663.4836, for $C_{39}H_{67}O_8$ (MH+)] and 2.5 mg of 16,19-mono-formaldehyde acetal derivative (15) of 13 [yield: 27.8 %, white wax, HRFABMS: obsd 651.4828, calcd 651.4836, for $C_{38}H_{67}O_8$ (MH+)]; $^1$H NMR: of 14 and 15: see Table 20.

24,28-S- and R-MTPA esters of 15: White oil-like; $^1$H NMR: see Table 20.

24,28-formaldehyde acetal derivative of squamocin (17): 65 mg of squamocin (16) was converted into 17 mg of 17 (yield: 28.3%) as a white oil; HRFABMS: obsd 635.4842, calcd 635.4887, for $C_{38}H_{67}O_7$ (MH+); $^1$H NMR: see Table 21.

15-TMSi derivative of 17: EIMS m/z (rel. int. %) 573 (5.6), 543(10.1), 507(15.2), 455 (79.4), 437 (13.7), 435 (10.9), 367 (100.0), 365 (21.5), 361(23.1), 339 (6.5), 309 (13.9), 293(13.2), 269(4.6), 252(19.0), 199(7.2), 185(12.4), 169(27.0).

15-S- and R-MTPA esters of 17: White oil-like; $^1$H NMR: see Table 21.

Formaldehyde acetal derivatives of gigantetrocin A: 60 mg of gigantetrocin A (10) was converted into 2.4 mg of 14,17-formaldehyde acetal derivative (11) of 13 [yield: 4.0%, white wax, HRFABMS: obsd 609.4730, calcd 609.4730, for $C_{36}H_{65}O_7$ (MH+)] and 21 mg of 17,18-formaldehyde acetal derivative (12) of 10 [yield: 35.0%, white wax, HRFABMS: obsd 609.4714, calcd 609.4730, for C36H6507 (MH1)]; $^1$H NMR: of 11 and 12 see Table 22; $^{13}$C NMR of 21693.8 (C-36, acetal carbon), 81.6 (C-18), 81.5 (C-17).

4,18-TMSi derivative of 11: EIMS m/z (rel. int. %) 737(8.8), 707(8.0), 641(3.8), 617(4.8), 551(3.0), 496(21.2), 461 (22.6), 453 (12.6), 426(43.2), 423(7.7), 369(18.0), 363 (8.2), 353(100.0), 309(24.6), 299(84.2), 263(13.8), 245 (19.3), 213(48.2).

4,14-TMSi derivative of 12: EIMS m/z (rel. int. %) 753(5.9, MH+), 737(6.7), 707 (2.0), 663(5.3), 617(3.2), 426(84.6), 399(7.2), 383 (28.7), 369 o30), 353(100.0), 336 (10.7), 309(64.5), 295(7.4), 281(18.1), 279(18.8), 263(19.7), 245(26.0), 243(18.8), 213 (32.4), 184(58.4).

4,14-S- and R-MTPA esters of 12: White oil-like; $^1$H NMR: see Table 22.

10,13-Formaldehyde acetal derivative of goniothalamicin (9): 50 mg of goniothalamicin (8) was converted into 16 mg of 9 (yield: 32.0%) as a white wax; HRFABMS: obsd 609.4730, calcd 609.4730, for C36H6507 (MH1); $^1$H NMR: see Table 23, $^{13}$C NMR 695.2 (C-36, acetal carbon), 81.1 (C-13), 80.0 (C-10).

4,18-TMSi derivative of 9: EIMS m/z (rel. int. %) 737 (1.2), 707(2.7), 641 (5.9), 541(4.2), 524(12.5), 496(8.7), 453 (13.5), 425 (41.0), 423 (16.0), 385 (15.4), 383 (8.8), 369 (22.8), 353(24.0), 299(87.7), 213(33.5).

4,18-S- and R-MTPA esters of 9: White oil-like; $^1$H NMR: see Table 23.

Mitochondrial Inhibition Assay Theory

The oxidative phosphorylation pathway (or electron transport chain) is responsible for oxidizing NADH to NAD$^+$ and producing ATP from ADP and phosphate within the mitochondria. There are five enzyme complexes in this pathway: NADH-ubiquinone reductase (complex I), succinate-ubiquinone reductase (complex II), ubiquinone-cytochrome c reductase (complex III), cytochrome c oxidase (complex IV) and the $F_0F_1$-ATPase complex (complex V). The end point of the oxidative phosphorylation pathway is the reduction of oxygen ($O_2$) to water in the mitochondria (thus, it is also called respiration), coupled with the synthesis of ATP by complex V. State 4 respiration is the oxidation of substrates in the absence of a phosphate acceptor (e.g., ADP). State 3 respiration occurs when a phosphate acceptor is present and oxygen utilization increases. The ratio of State 3 respiration to State 4 respiration is the respiratory control ratio (RCR).

The process of respiration can be measured by using an oxygen electrode to detect the amount of oxygen present in the assay cell. If respiration is occurring normally, the concentration of oxygen should slowly decrease as it is reduced to water. However, if there is some type of inhibition of oxidative phosphorylation occurring, the oxygen level will no longer decrease at the same rate. This rate of oxygen usage can be visualized by a chart recorder connected to the oxygen electrode. At normal respiration, a decreasing baseline slope will be established. During inhibition, however, the baseline slope should decrease (i.e., the slope will move closer to zero), since the oxygen present is no longer being reduced. In other words, the oxygen concentration in the assay cell is no longer decreasing at the same rate as in normal respiration. Furthermore, inhibition sites at specific complexes can be determined by competitive inhibition studies. This is accomplished by addition of a known inhibitor of, e.g., complex I, followed by the new respiration-inhibiting compound. If the new compound does not change the effect of the known inhibitor, it can be assumed that they are acting at the same site. This can be verified by trying inhibitors at other sites and by reversing the order, i.e., adding the new compound and then the known inhibitor.

Materials

Trizma base (Tris[hydroxymethyl]aminomethane), DL-malic acid, L-glutamic acid (monopotassium salt), adenosine 5'-diphosphate (potassium salt; from yeast ATP) and rotenone (6αβ-4'5'-tetrahydro-2,3-dimethoxy-5'β-isopropenyl-furano-(3',2',8,9)-6H-rotoxen-12-one) were purchased from Sigma Chemical Company. EDTA ([ethylenedinitrilo)-tetraacetic acid disodium salt]) was purchased from Fisher Scientific. Sucrose and potassium chloride were purchased from Mallinckrodt, and potassium phosphate (potassium dihydrogen phosphate), monobasic, was purchased from J. T. Baker. The dye and bovine serum albumin (BSA) for the Bradford protein determination assay were purchased from Bio-Rad as an assay kit.

Mitochondrial Isolation

The method for isolating rat liver mitochondria essentially followed the published methodology. Ahammadsahib et al., *Life Sciences*, 53, pgs. 1113–1120 (1993). The isolation buffer used for the isolation of mitochondria from rat liver consisted of 4 mM Tris-HCl, 0.5 mM EDTA, and 250 mM sucrose at a pH of 7.4. The isolation buffer was kept at refrigeration temperature at all times by storing on ice during the whole procedure. The rats were supplied by Sprague-Dawley, were male, and weighed approximately 300–320 grams. They were sacrificed with carbon dioxide, and the livers were removed and immediately placed in the isolation buffer on ice. The livers were then rinsed with several washings of cold buffer, cut into pieces, and homogenized. The homogenates were then centrifuged (Sorvall Superspeed RC2-B, 4° C.) for 10 minutes at approximately 2000 rpms; the supernatant was next centrifuged for 20 minutes at approximately 9000 rpms. The pellet was reserved and resuspended in 2 ml of assay buffer with a glass pipet. The assay buffer consisted of 100 mM KCl, 5 mM $KH_2PO$, 1 mM EDTA, 5 mM glutamate, 1 mM malate, and 20 mM Tris-HCl at a pH of 7.4 and was stored at room temperature.

Protein Determination

The protein concentration of the mitochondrial sample was determined using the Bradford Assay. Bovine serum albumin was used as a standard, and three replicates of five different concentrations represented the standard curve. Three replicates of 1 µl and 2 µl were tested for mitochondrial sample, with the result from the 2 µl sample used to determine the protein content. Absorption was determined at 595 nm using a Beckman DU-7 Spectrophotometer.

Mitochondrial Inhibition Assay

Respiration was monitored polarographically with an oxygen electrode and a biological oxygen monitor. The mitochondrial assay was initiated by allowing 2.9 ml of assay buffer to equilibrate the approximately 5 minutes. The system was kept at a constant temperature of 30° C. by a water-bath circulator. The mitochondrial sample (0.1 ml) was added, the solution was equilibrated for 1 minute, and the electrode was inserted. After the initial State 4 respiration had stabilized (as indicated by a consistent slope on the chart recorder), 5 µl of a 0.05M ADP solution was added, and State 3 and State 4 respirations were allowed to stabilize. Next, 10 µl of the freshly prepared acetogenin solution (in 95% ethanol) was injected, and the solution was allowed to equilibrate for 2 minutes. After equilibration, 5 µl of ADP was added, again letting State 3 and State 4 respirations occur. Once either State 4 had stabilized or 2 minutes had passed, the recording was discontinued. Two to three replicates at each concentration of the acetogenin of interest were conducted, depending on the amount of mitochondrial suspension available. State 3 and State 4 respirations were measured by determining the slope of each; if a straight line for State 4 was difficult to determine, the line was determined as the change of slope just following State 3 respiration.

We claim:

1. An intramolecular cyclic formaldehyde acetal of an acetogenin selected from the group consisting of bullatalicin, bullatanocin, bullatanocinone, bullatalicinone, asiminacin, squamocin, squamostatin A, gigantetronenin, gigantecin, C 18/21 cis-gigantecin, gigantetrocin, and goniothalamicin and acetylated derivatives thereof.

2. The cyclic acetal of claim 1 wherein the acetogenin is selected from the group consisting of bullatalicin, bullatanocin, bullatanocinone, bullatalicinone, squamocin, squamostatin A, gigantetrocin, and goniothalamicin.

* * * * *

UNITED STATES PATENT AND TRADEMARK OFFICE
CERTIFICATE OF CORRECTION

PATENT NO. : 5,717,113
DATED : February 10, 1998
INVENTOR(S) : Jerry McLaughlin et al.

It is certified that error appears in the above-identified patent and that said Letters Patent is hereby corrected as shown below:

Column 1, line 6, insert the following:

--<u>Government Rights</u>
This invention was made with United States Government support under Grant No. CA30909, awarded by the NIH. The United States Government has certain rights to the invention.--

Signed and Sealed this

Sixteenth Day of February, 1999

Attest:

Attesting Officer

*Acting Commissioner of Patents and Trademarks*